(12) United States Patent
Qin et al.

(10) Patent No.: US 8,507,532 B2
(45) Date of Patent: Aug. 13, 2013

(54) STABLE INSECTICIDE COMPOSITIONS AND METHODS FOR PRODUCING SAME

(75) Inventors: Kuide Qin, Westfield, IN (US); Raymond E. Boucher, Jr., Lebanon, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 538 days.

(21) Appl. No.: 12/653,996

(22) Filed: Dec. 22, 2009

(65) Prior Publication Data

US 2010/0168178 A1 Jul. 1, 2010

Related U.S. Application Data

(60) Provisional application No. 61/203,600, filed on Dec. 26, 2008.

(51) Int. Cl.
*A61K 31/44* (2006.01)

(52) U.S. Cl.
USPC ............................ 514/336; 514/277; 514/357

(58) Field of Classification Search
USPC ......................................... 514/336, 277, 357
See application file for complete search history.

(56) References Cited

U.S. PATENT DOCUMENTS

| 7,511,149 | B2 | 3/2009 | Arndt et al. |
|---|---|---|---|
| 7,604,815 | B2 | 10/2009 | Loso et al. |
| 7,678,920 | B2 | 3/2010 | Zhu et al. |
| 7,687,634 | B2 | 3/2010 | Loso et al. |
| 7,705,154 | B2 | 4/2010 | Heller et al. |
| 7,705,156 | B2 | 4/2010 | Loso et al. |
| 7,709,648 | B2 | 5/2010 | Meyer et al. |
| 7,709,649 | B2 | 5/2010 | Zhu et al. |
| 7,754,888 | B2 | 7/2010 | Loso et al. |
| 2005/0228027 | A1 | 10/2005 | Zhu et al. |
| 2007/0299264 | A1 | 12/2007 | Huang et al. |
| 2008/0033180 | A1 | 2/2008 | Renga et al. |
| 2008/0058390 | A1 | 3/2008 | Loso et al. |
| 2008/0108665 | A1 | 5/2008 | Huang et al. |
| 2008/0108666 | A1 | 5/2008 | Loso et al. |
| 2008/0108667 | A1 | 5/2008 | Zhu et al. |
| 2008/0132705 | A1 | 6/2008 | Heller et al. |
| 2008/0194634 | A1 | 8/2008 | Arndt et al. |
| 2008/0194830 | A1 | 8/2008 | Meyer et al. |
| 2008/0280915 | A1 | 11/2008 | Loso et al. |
| 2009/0006670 | A1 | 1/2009 | Guok et al. |
| 2009/0006676 | A1 | 1/2009 | Sampat et al. |
| 2010/0144794 | A1 | 6/2010 | Loso et al. |
| 2010/0144803 | A1 | 6/2010 | Loso et al. |
| 2010/0152245 | A1 | 6/2010 | Loso et al. |
| 2010/0179099 | A1 | 7/2010 | Loso et al. |
| 2011/0160054 | A1 * | 6/2011 | Breuningger et al. ........ 504/100 |

FOREIGN PATENT DOCUMENTS

| WO | WO 2007/095229 A2 | 8/2007 |
|---|---|---|
| WO | WO 2007/149134 A1 | 12/2007 |
| WO | 2008106006 A1 | 9/2008 |
| WO | WO 2009/062905 A1 | 5/2009 |
| WO | WO 2009/134224 A1 | 11/2009 |
| WO | WO 2009/135613 A1 | 11/2009 |
| WO | WO 2009/135613 A1 | 11/2009 |

OTHER PUBLICATIONS

Breumingger etal. U.S. Appl. No. 61/092,552 (p. 2), Aug. 28, 2008.*
Notification of Transmittal of the International Preliminary Report on Patentability; Mailed Apr. 3, 2011; PCT/US2009/006670.
Notification of Transmittal of the International Preliminary Report on Patentability; Mailed Apr. 3, 2011; PCT/US2009/006676.
Kagabu, Shinzo and Medej, Somporn; "Stability Comparison of Imidacloprid and Related Compounds under Simulated Sunlight, Hydrolysis Conditions, and to Oxygen;" Biosch, Biotech, Biochem, 59 (6), 980-985, 1995.
Barton et al.; "Sulphoximides", Comprehensive Organic Chemistry, 1979, Pergamon Press, XP002576300, ISBN 0080213154, vol. 3, pp. 227-232, p. 229, paragraph 2, p. 230, paragraph 1.
International Search Report and Written Opinion of the International Searching Authority; PCT/US2009/006670, 2009.
International Search Report and Written Opinion of the International Searching Authority; PCT/US2009/06676, 2009.
International Search Report and Written Opinion of the International Searching Authority; PCT/US2007/003781, 2007.
Morrison et al.; Stereochemistry I. Stereoisomers; Organic Chemistry; Chapter 4; 1987.

* cited by examiner

*Primary Examiner* — Rei-tsang Shiao
(74) *Attorney, Agent, or Firm* — Carl D. Corvin; Krieg DeVault LLP

(57) ABSTRACT

Insect controlling compositions including an N-substituted (6-haloalkylpyridin-3-yl)alkyl sulfoximine compound exhibiting increased stability, along with methods for preparing same, are disclosed.

3 Claims, No Drawings

STABLE INSECTICIDE COMPOSITIONS AND METHODS FOR PRODUCING SAME

CROSS-REFERENCE TO RELATED APPLICATIONS

The present application claims priority to U.S. Provisional Patent Application No. 61/203,600 filed Dec. 26, 2008, the content of which is incorporated herein by reference in its entirety.

FIELD OF THE INVENTION

The invention disclosed in this document is related to the field of pesticides and their use in controlling pests.

BACKGROUND OF THE INVENTION

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

Many pesticide compositions have been developed over time to destroy pests and alleviate the damages they cause. With respect to at least some of these compositions, physical and chemical instabilities can lead to a reduction in pesticidal activity of the composition and/or present complications when it comes time to apply the composition to a locus where pest control is necessary or desired. For example, physical and chemical instabilities can alter one or more properties of the composition which make it difficult or impossible to prepare appropriate solutions of the composition for use. More particularly, many pesticide compositions are provided in a concentrated formulation from the manufacturer and are subsequently diluted by an end user before their application. During the time between manufacture and application, liquid forms of pesticide compositions can solidify as a result of chemical and physical instabilities of the composition. Often times, this solidification prevents or substantially impedes the dispersion of the composition into a solution suitable for application, resulting in greater user burden and cost and/or wasted pesticide products. Moreover, when physical and chemical instabilities lead to a reduction in pesticidal activity of a composition, an increase in the concentration at which the pesticide is applied and/or more frequent applications of the pesticide composition are often required. As a result, user costs and the cost to consumers can escalate. Therefore, a need exists for new pesticide compositions that exhibit increased chemical and physical stability properties.

U.S. Patent Application Publication 2007/0203191 A1 describes certain N-substituted (6-haloalkylpyridin-3-yl) alkyl sulfoximine compounds and their use in controlling insects. It has now been discovered how to improve the stability of compositions including one or more of these compounds over greater periods of time.

SUMMARY OF THE INVENTION

The present invention concerns novel compositions including an N-substituted (6-haloalkylpyridin-3-yl)alkyl sulfoximine compound and exhibiting increased stability, along with their use in controlling insects and certain other invertebrates, particularly aphids and other sucking insects. This invention also includes new synthetic procedures for preparing the compositions and methods of controlling insects using the compositions.

This invention concerns compositions useful for the control of insects, especially useful for the control of aphids and other sucking insects, along with methods for preparing same. More specifically, in one embodiment, a method includes providing a composition including a first ratio between stereoisomers of a compound having the formula (I)

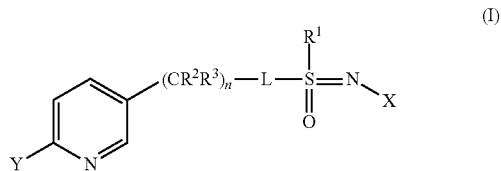

(I)

wherein
X represents $NO_2$, CN or $COOR^4$;
L represents a single bond or $R^1$, S and L taken together represent a 4-, 5- or 6-membered ring;
$R^1$ represents ($C_1$-$C_4$) alkyl;
$R^2$ and $R^3$ are distinct from each other and individually represent hydrogen, methyl, ethyl, fluoro, chloro or bromo;
n is 1 when L represents a single bond and is 0 when $R^1$, S and L taken together represents a 4-, 5- or 6-membered ring;
Y represents ($C_1$-$C_4$) haloalkyl, F, Cl, Br, or I; and
$R^4$ represents ($C_1$-$C_3$) alkyl.

The method also includes heating the composition in a manner effective to provide a second, distinct ratio between the stereoisomers.

In one particular form of the method, the composition includes a compound of formula (I) wherein L represents a single bond, i.e., having the following structure wherein n is 1

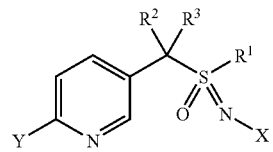

wherein
X represents $NO_2$, CN or $COOR^4$;
$R^1$ represents ($C_1$-$C_4$) alkyl;
$R^2$ and $R^3$ are distinct from each other and individually represent hydrogen, methyl, ethyl, flouro, chloro or bromo;
Y represents ($C_1$-$C_4$) haloalkyl, F, Cl, Br, or I; and
$R^4$ represents ($C_1$-$C_3$) alkyl.

In another particular form of the method, the composition includes a compound of formula (I) wherein $R^1$, S and L taken together form a saturated 5-membered ring, and n is 0, i.e., having the structure

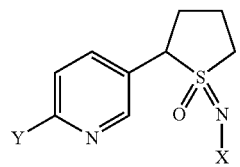

wherein

X represents NO$_2$, CN or COOR$^4$;

Y represents (C$_1$-C$_4$) haloalkyl, F, Cl, Br, or I; and

R$^4$ represents (C$_1$-C$_3$) alkyl.

In yet other forms of the method, the composition includes compounds of formula (I) in one or more of the following classes:

(1) Compounds of formula (I) wherein X is NO$_2$ or CN, most preferably CN.

(2) Compounds of formula (I) wherein Y is CF$_3$.

(3) Compounds of formula (I) wherein R$^2$ and R$^3$ are distinct from each other and independently represent hydrogen, methyl or ethyl.

(4) Compounds of formula (I) wherein R$^1$ represents CH$_3$.

It will be appreciated by those skilled in the art that one or more of the compositions described herein may be comprised of combinations of the above described classes of the compound of formula (I).

In one form of the method, the heating is performed at a minimum of about 20° C. for at least about four hours. In another form, the heating is performed at a minimum of about 50° C. from about four to about seventy two hours.

In another embodiment, a method includes providing a composition which includes a stereoisomeric mixture of a compound having the following structure:

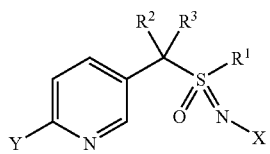

wherein

X represents NO$_2$, CN or COOR$^4$;

R$^1$ represents (C$_1$-C$_4$) alkyl;

R$^2$ and R$^3$ are distinct from each other and individually represent hydrogen, methyl, ethyl, fluoro, chloro or bromo;

Y represents (C$_1$-C$_4$) haloalkyl, F, Cl, Br, or I;

R$^4$ represents (C$_1$-C$_3$) alkyl; and the mixture is defined by a first pair of diastereomers and a second pair of diastereomers.

The method also includes heating the composition to convert at least a portion of the second pair of diastereomers to the first pair of diastereomers.

In another embodiment, a composition includes a stereoisomeric mixture of {1-[6-(trifluoromethyl)pyridin-3-yl] ethyl}(methyl)oxido-λ$^4$-sulfanylidenecyanamide defined by a first pair of diastereomers and a second pair of diastereomers, wherein the first and second pairs of diastereomers are present at a ratio of at least about 3:1. In one form, the first and second pairs of diastereomers are present at a ratio from about 3:1 to 100:1. In another form, the first and second pairs of diastereomers are present at a ratio from about 3:1 to 40:1.

In yet another embodiment, a method includes applying to a locus where control is desired an insect-inactivating amount of a pesticide composition.

Still, further embodiments, forms, features, aspects, benefits, objects, and advantages of the present invention shall become apparent from the detailed description and examples provided.

Substituents (Non-Exhaustive List)

The examples given for the substituents are (except for halo) non-exhaustive and must not be construed as limiting the invention disclosed in this document.

"alkyl" (including derivative terms such as alkoxy) means straight chain, branched chain and cyclic groups including, for example, methyl, ethyl, 1-methylethyl, propyl, 1,1-dimethylethyl and cyclopropyl.

"alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"aryl" means a cyclic, aromatic substituent consisting of hydrogen and carbon, for example, phenyl, naphthyl, and biphenylyl.

"halo" means fluoro, chloro, bromo, and iodo.

"haloalkyl" means an alkyl group substituted with from one to the maximum possible number of halogen atoms, all combinations of halogens included.

DETAILED DESCRIPTION OF THE INVENTION

Throughout this document, all temperatures are given in degrees Celsius, and all percentages are weight percentages unless otherwise stated.

The compounds of formula (Ia), wherein R$^1$, R$^2$, R$^3$, R$^4$, X, and Y are as previously defined, L is a single bond and n is 1, can be prepared by the methods illustrated in Scheme A:

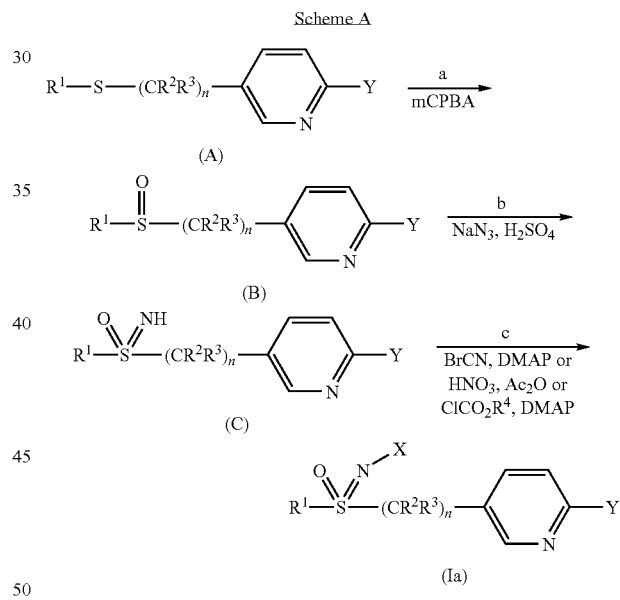

In step a of Scheme A, sulfide of formula (A) is oxidized with meta-chloroperoxybenzoic acid (mCPBA) in a polar solvent below 0° C. to provide sulfoxide of formula (B). In most cases, dichloromethane is the preferred solvent for oxidation.

In step b of Scheme A, sulfoxide (B) is iminated with sodium azide in the presence of concentrated sulfuric acid in an aprotic solvent under heating to provide sulfoximine of formula (C). In most cases, chloroform is the preferred solvent for this reaction.

In step c of Scheme A, the nitrogen of sulfoximine (C) can be either cyanated with cyanogen bromide in the presence of a base, or nitrated with nitric acid in the presence of acetic anhydride under mildly elevated temperature, or carboxylated with alkyl (R4) chloroformate in the presence of base such as 4-dimethylaminopyridine (DMAP) to provide N-substitutedsulfoximine (Ia). Base is required for efficient cyanation and carboxylation and the preferred base is DMAP, whereas sulfuric acid is used as catalyst for efficient nitration reaction.

The compounds of formula (Ia), wherein X represents CN and $R^1$, $R^2$, $R^3$, $R^4$ and Y are as previously defined and n is 1, can be prepared by the mild and efficient method illustrated in Scheme B.

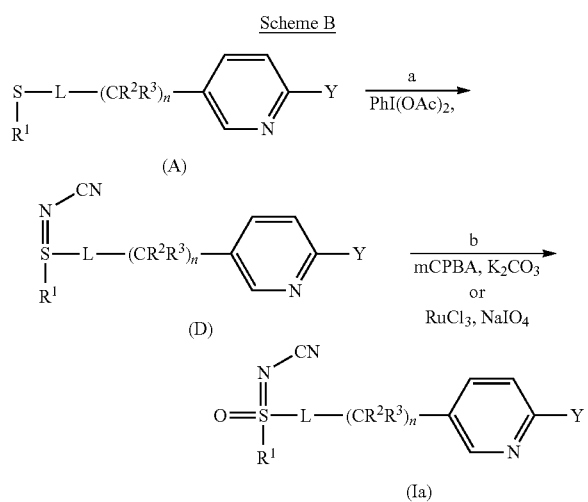

In step a of Scheme B, sulfide is oxidized with iodobenzene diacetate in the presence of cyanamide at 0° C. to give sulfilimine (D). The reaction can be carried out in a polar aprotic solvent like $CH_2Cl_2$.

In step b of Scheme B, the sulfilimine (D) is oxidized with mCPBA. A base such as potassium carbonate is employed to neutralize the acidity of mCPBA. Protic polar solvents such as ethanol and water are used to increase the solubility of the sulfilimine starting material and the base employed. The sulfilimine (D) can also be oxidized with aqueous sodium or potassium periodinate solution in the presence of catalyst ruthenium trichloride hydrate or similar catalyst. The organic solvent for this catalysis can be polar aprotic solvent such as $CH_2Cl_2$, chloroform, or acetonitrile.

The α-carbon of the N-substituted sulfoximine of formula (Ia), i.e., n=1, $R^3$=H in the $(CR^2R^3)$ group adjacent to the N-substituted sulfoximine function can be further alkylated or halogenated ($R^5$) in the presence of a base such as potassium hexamethyldisilamide (KHMDS) to give N-substituted sulfoximines of formula (Ib), wherein $R^1$, $R^2$, $R^3$, $R^4$, X, L and Y are as previously defined and Z is an appropriate leaving group, as illustrated in Scheme C. The preferred leaving groups are iodide ($R^5$=alkyl), benzenesulfonimide ($R^5$=F), tetrachloroethene ($R^5$=Cl), and tetrafluoroethene ($R^5$=Br).

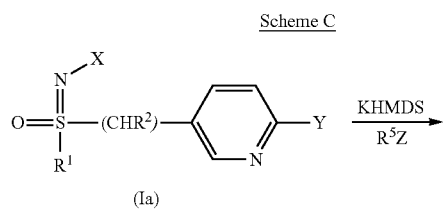

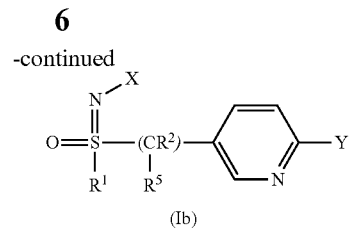

The starting sulfides (A) in Scheme A can be prepared in different ways as illustrated in Schemes D, E, F, G and H.

In Scheme D, the sulfide of formula $(A_1)$, wherein $R^1$, $R^2$ and Y are as previously defined, n=1, and $R^3$=H, can be prepared from the chloride of formula (D) by nucleophilic substitution with the sodium salt of an alkyl thiol.

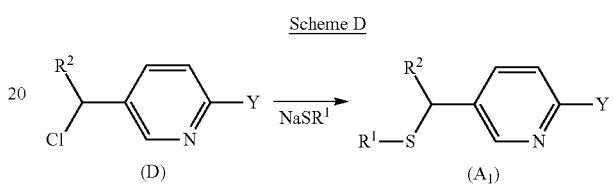

In Scheme E, the sulfide of formula $(A_4)$, wherein $R^1$, S and L taken together represents a 4-, 5- or 6-membered ring (m=0, 1, or 2) and n is 0 can be prepared from the corresponding substituted chloromethylpyridine by treatment with thiourea, hydrolysis and subsequent alkylation with the appropriate bromo chloroalkane (m=0, 1, or 2) under aqueous base conditions, and cyclization in the presence of a base like potassium-t-butoxide in a polar aprotic solvent such as THF.

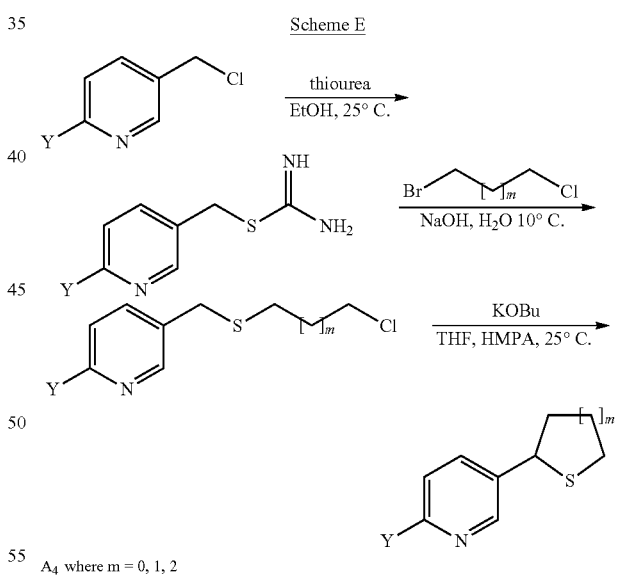

$A_4$ where m = 0, 1, 2

Sulfides of formula $(A_1)$, wherein $R^1$, $R^2$=$CH_3$, Y as previously defined, and $R^3$=H, can be prepared alternatively via methods illustrated in Scheme F. Accordingly, the appropriate enone is coupled with dimethyl-aminoacrylonitrile and cyclized with ammonium acetate in DMF to yield the corresponding 6-substituted nicotinonitrile. Treatment with methylmagnesium bromide, reduction with sodium borohydride, chlorination with thionyl chloride, and nucleophilic substitution with the sodium salt of an alkyl thiol provide desired sulfides $(A_1)$.

Scheme F

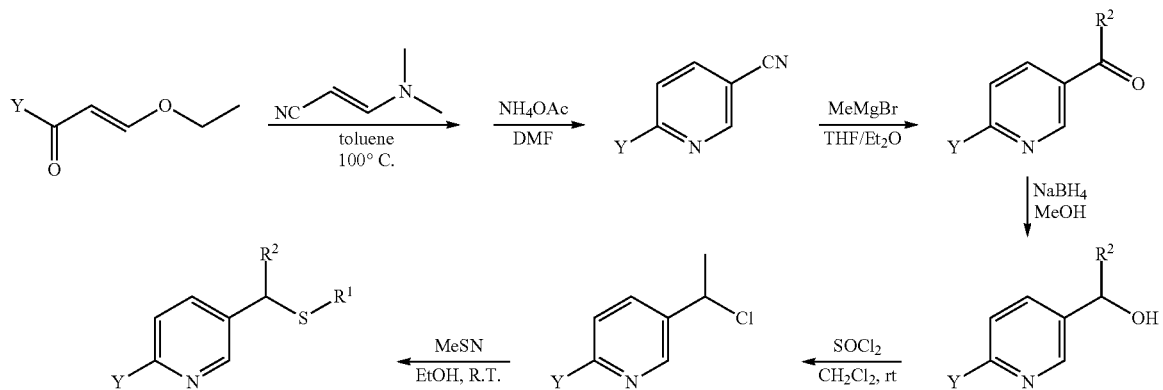

Sulfides of formula (A₁), wherein R¹=methyl or ethyl, R² and R³ are distinct from each other and independently represent hydrogen, methyl or ethyl, and Y is as previously defined can be prepared via a variation of Scheme F, depicted in Scheme G, wherein enamines, formed from the addition of an amine, e.g., pyrrolidine, with the Michael adduct of certain sulfides with appropriately substituted α,β-unsaturated aldehydes, are coupled with substituted enones and cyclized with ammonium acetate in acetonitrile to yield the desired sulfides (A₁).

Scheme G

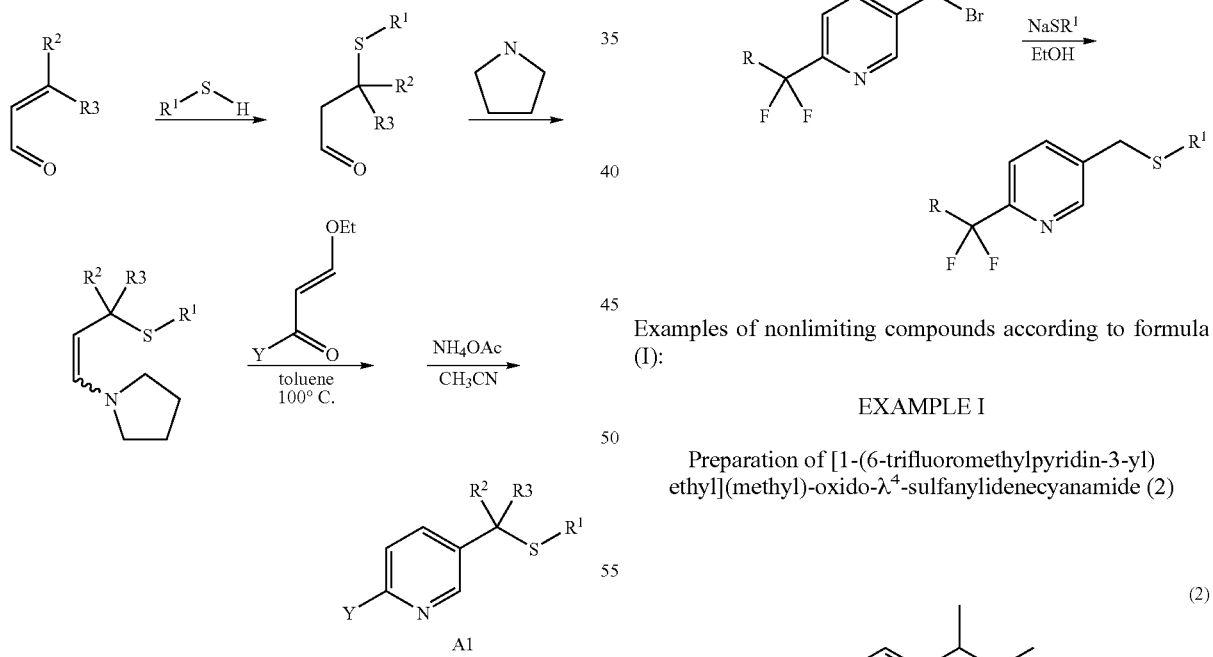

In Scheme H, sulfides of formula (A₁), wherein Y is a fluoroalkyl group, R¹, R² and R³ are as previously defined, and n=1 can be prepared from the 6-acylpyridine or 6-formyl pyridine by reaction with diethylaminosulfur trifluoride (DAST). Subsequent halogenation of the 3-methyl group with NBS followed by nucleophilic substitution with the sodium salt of an alkyl thiol furnishes the desired sulfide.

Scheme H

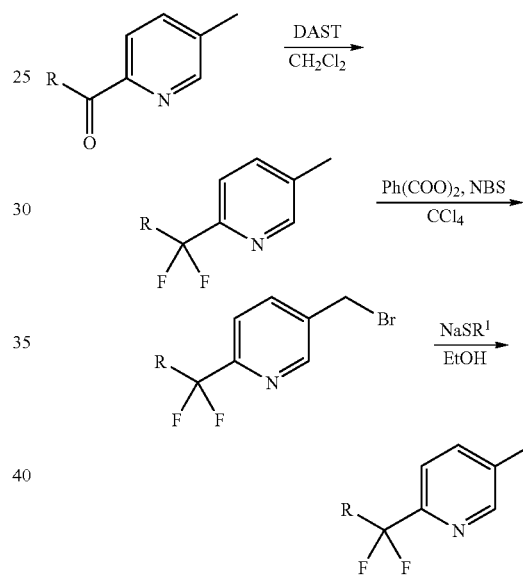

Examples of nonlimiting compounds according to formula (I):

EXAMPLE I

Preparation of [1-(6-trifluoromethylpyridin-3-yl)ethyl](methyl)-oxido-λ⁴-sulfanylidenecyanamide (2)

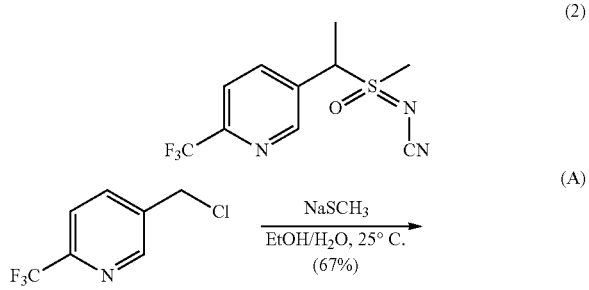

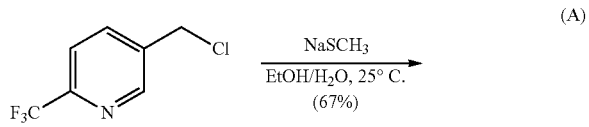

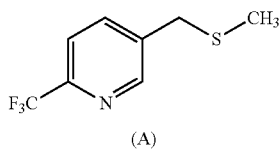

(A)

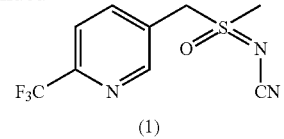

(1)

To a solution of 3-chloromethyl-6-(trifluoromethyl)pyridine (5.1 g, 26 mmol) in dimethyl sulfoxide (DMSO; 20 mL) was added in one portion sodium thiomethoxide (1.8 g, 26 mmol). A violent exothermic reaction was observed which resulted in the reaction turning dark. The reaction was stirred for 1 hr, then additional sodium thiomethoxide (0.91 g, 13 mmol) was added slowly. The reaction was stirred overnight, after which it was poured into $H_2O$ and several drops of conc. HCl were added. The mixture was extracted with $Et_2O$ (3×50 mL) and the organic layers combined, washed with brine, dried over $MgSO_4$ and concentrated. The crude product was purified by chromatography (Prep 500, 10% acetone/hexanes) to furnish the sulfide (A) as a pale yellow oil (3.6 g, 67%). $^1$H NMR (300 MHz, $CDCl_3$) δ 8.6 (s, 1H), 7.9 (d, 1H), 7.7 (d, 1H), 3.7 (s, 2H), 2.0 (s, 3H); GC-MS: mass calcd for $C_8H_8F_3NS$ [M]$^+$ 207. Found 207.

To a solution of m-chloroperbenzoic acid (mCPBA; 80 percent, 1.0 g, 4.9 mmol) in EtOH (10 mL) at 0° was added a solution of $K_2CO_3$ (1.4 g, 10 mmol) in $H_2O$ (7 mL). The solution was stirred for 20 min, then a solution of sulfilimine (B) (0.60 g, 2.4 mmol) in EtOH (20 mL) was added all at once. The reaction was stirred at 0° C. for 30 min, then allowed to warm to room temperature over the course of 1 hr. The reaction was then quenched with aq. sodium bisulfite and the mixture was concentrated to remove ethanol. The resulting mixture was extracted with $CH_2Cl_2$ and the combined organic layers dried over $MgSO_4$ and concentrated. The crude product was purified by chromatography (chromatotron, 50 percent acetone/hexanes) to furnish the sulfoximine (1) as an off-white solid (0.28 g, 44 percent). Mp=135-137° C.; $^1$H NMR (300 MHz, $CDCl_3$) δ 8.8 (s, 1H), 8.1 (d, 1H), 7.8 (d, 1H), 4.7 (m, 2H), 3.2 (s, 3H); LC-MS (ELSD): mass calcd for $C_9H_9F_3N_3OS$ [M+H]$^+$264.04. Found 263.92.

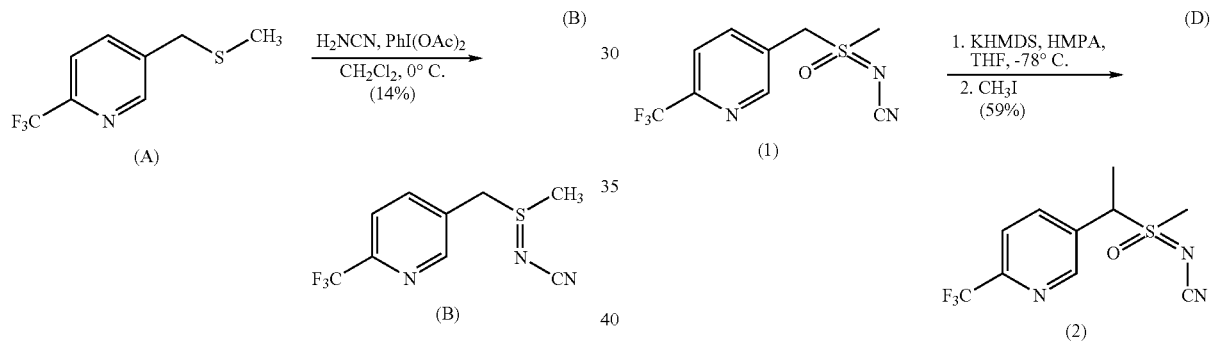

To a solution of sulfide (A) (3.5 g, 17 mmol) and cyanamide (1.4 mg, 34 mmol) in $CH_2Cl_2$ (30 mL) at 0° C. was added iodobenzenediacetate (11.0 g, 34 mmol) all at once. The reaction was stirred for 30 min, then allowed to warm to room temperature overnight. The mixture was diluted with $CH_2Cl_2$ (50 mL) and washed with $H_2O$. The aqueous layer was extracted with ethyl acetate (4×50 mL), and the combined $CH_2Cl_2$ and ethyl acetate layers dried over $MgSO_4$ and concentrated. The crude product was triturated with hexanes and purified by chromatography (chromatotron, 60 percent acetone/hexanes) to furnish the sulfilimine (B) as a yellow gum (0.60 g, 14 percent). IR (film) 3008, 2924, 2143, 1693 cm$^{-1}$; $^1$H NMR (300 MHz, $CDCl_3$) δ 8.8 (s, 1H), 8.0 (d, 1H), 7.8 (d, 1H), 4.5 (d, 1H), 4.3 (d, 1H), 2.9 (s, 3H); LC-MS (ESI): mass calcd for $C_9H_9F_3N_3S$ [M+H]$^+$248.04. Found 248.

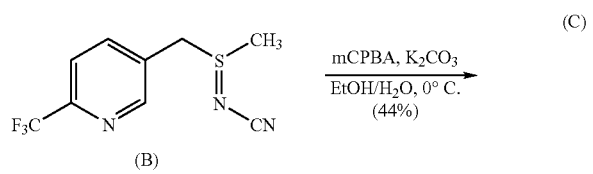

To a solution of sulfoximine (1) (50 mg, 0.19 mmol) and hexamethylphosphoramide (HMPA; 17 μL, 0.10 mmol) in tetrahydrofuran (THF; 2 mL) at −78° C. was added potassium hexamethyldisilazane (KHMDS; 0.5 M in toluene, 420 μL, 0.21 mmol) dropwise. The solution was stirred at −78° C. for an additional 20 min, after which iodomethane (13 μL, 0.21 mmol) was added. The reaction was allowed to warm to room temperature over the course of 1 hr, after which it was quenched with satd. aq. $NH_4Cl$ and extracted with $CH_2Cl_2$. The organic layer was dried over $Na_2SO_4$, concentrated, and the crude product purified by chromatography (chromatotron, 70 percent acetone/$CH_2Cl_2$) to furnish the sulfoximine (2) as a 2:1 mixture of diastereomers (colorless oil; 31 mg, 59 percent). Sulfoximine (2) is commonly known as sulfoxaflor, further details of which are available at http://www.alanwood.net/pesticides/index_cn_frame.html.

According to a revised version of IUPAC nomenclature, sulfoximine (2) is also referred to as [methyl(oxido){1-[6-(trifluoromethyl)-3-pyridyl]ethyl}-λ$^6$-sulfanylidene]cyanamide, and the CAS name given to sulfoximine (2) is N-[methyloxido[1-[6-(trifluoromethyl)-3-pyridinil]ethyl]-λ$^4$-sulfanylidene]cyanamide. $^1$H NMR (300 MHz, $CDCl_3$) δ (major diastereomer) 8.8 (s, 1H), 8.1 (d, 1H), 7.8 (d, 1H), 4.6 (q, 1H), 3.0 (s, 3H), 2.0 (d, 3H); (minor diastereomer) 8.8 (s, 1H), 8.1

(d, 1H), 7.8 (d, 1H), 4.6 (q, 1H), 3.1 (s, 3H), 2.0 (d, 3H); LC-MS (ELSD): mass calcd for $C_{10}H_{10}F_3N_3OS$ [M+H]$^+$ 278.06. Found 278.05.

EXAMPLE II

Preparation of 2-(6-trifluoromethylpyridin-3-yl)-1-oxido-tetrahydro-1H-1λ$^4$-thien-1-ylidenecyanamide (3)

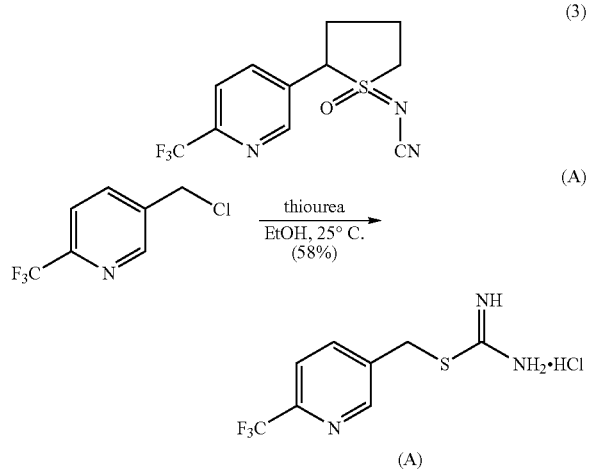

To a suspension of thiourea (1.2 g, 16 mmol) in EtOH (25 mL) was added a solution of 3-chloromethyl-6-(trifluoromethyl)pyridine in EtOH (10 mL). The suspension was stirred at room temperature for 2 days, during which a white precipitate formed. The precipitate was filtered to give the desired amidine hyrdochloride as a white solid (2.4 g, 58 percent). Mp=186-188° C. No further attempt was made to purify the product. $^1$H NMR (300 MHz, CDCl$_3$) δ 8.9 (bs, 4H), 8.4 (s, 1H), 7.6 (d, 1H), 7.3 (d, 1H), 4.2 (s, 2H); LC-MS (ELSD): mass calcd for $C_8H_8FN_3S$ [M+H]$^+$236.05. Found 236.01.

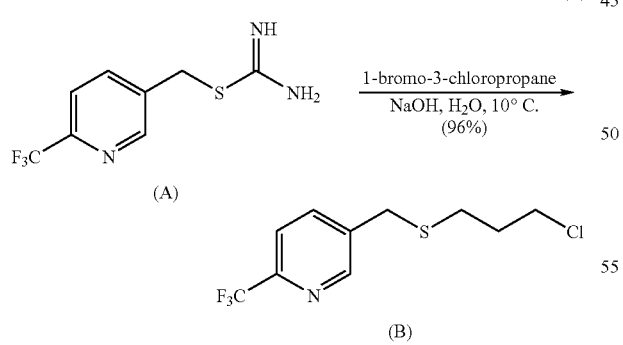

To a solution of amidine hydrochloride (A) (1.8 g, 6.8 mmol) in H$_2$O (12 mL) at 10° C. was added 10 N NaOH (0.68 mL, 6.8 mmol), which resulted in the formation of a white precipitate. The suspension was heated at 100° C. for 30 min, then cooled back down to 10° C. Additional 10 N NaOH (0.68 mL, 6.8 mmol) was then added, followed by 1-bromo-3-chloropropane (0.67 mL, 6.8 mmol) all at once. The reaction was stirred at room temperature overnight, then extracted with CH$_2$Cl$_2$. The combined organic layers were washed with brine, dried over Na$_2$SO$_4$ and concentrated to furnish the sulfide (B) as a colorless oil (1.7 g, 96 percent). No further attempt was made to purify the product. $^1$H NMR (300 MHz, CDCl$_3$) δ 8.6 (s, 1H), 7.8 (d, 1H), 7.6 (d, 1H), 3.8 (s, 2H), 3.6 (t, 2H), 2.6 (t, 2H), 2.0 (quint, 2H).

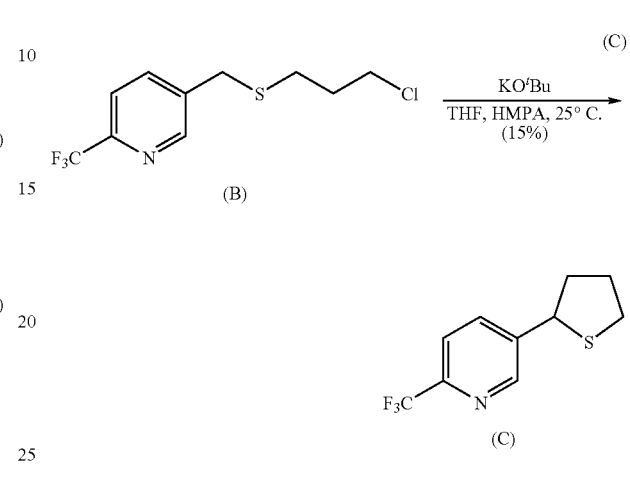

To a suspension of potassium tert-butoxide (1.5 g, 13 mmol) in THF (12 mL) was added HMPA (1.7 mL, 10 mmol) followed by a solution of sulfide (B) (1.8 g, 6.7 mmol) in THF (3 mL) dropwise. The reaction was allowed to stir at room temperature overnight, followed by concentration and purification by chromatography (Biotage, 40 percent EtOAc/hexanes) to furnish cyclized product (C) as an orange oil (230 mg, 15 percent). $^1$H NMR (300 MHz, CDCl$_3$) δ 8.7 (s, 1H), 8.0 (d, 1H), 7.6 (d, 1H), 4.6 (dd, 1H), 3.2 (m, 1H), 3.1 (m, 1H), 2.5 (m, 1H), 2.3 (m, 1H), 2.1-1.9 (m, 2H).

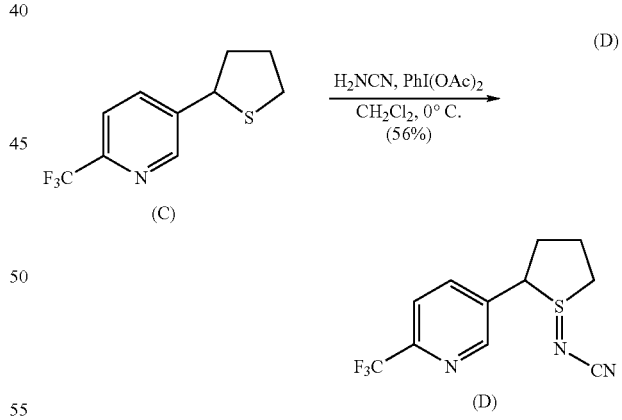

To a solution of sulfide (C) (230 mg, 0.99 mmol) and cyanamide (83 mg, 2.0 mmol) in CH$_2$Cl$_2$ (5 mL) at 0° C. was added iodobenzenediacetate (350 mg, 1.1 mmol) all at once. The reaction was stirred for 3 hr, then concentrated and the crude product purified by chromatography (chromatotron, 50 percent acetone/hexanes) to furnish the sulfilimine (D) as an orange oil (150 mg, mixture of diastereomers, 56 percent). $^1$H NMR (300 MHz, CDCl$_3$) δ 8.8 (s, 1H), 7.9 (d, 1H), 7.8 (d, 1H), 4.8 (dd, 1H), 3.5 (m, 2H), 2.9-2.7 (m, 2H), 2.6 (m, 1H), 2.3 (m, 1H).

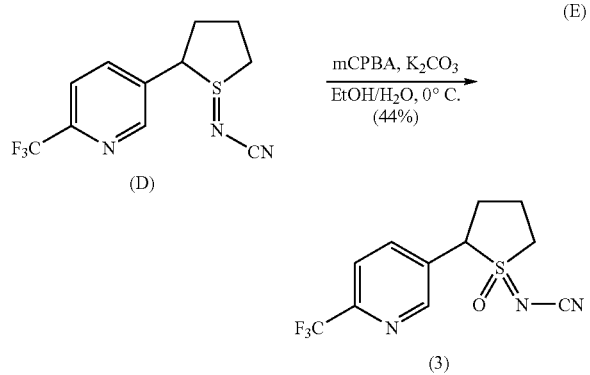

To a solution of mCPBA (80 percent, 180 mg, 0.82 mmol) in EtOH (3 mL) at 0° C. was added a solution of $K_2CO_3$ (230 mg, 1.7 mmol) in $H_2O$ (1.5 mL). The solution was stirred for 20 min, then a solution of sulfilimine (D) (150 mg, 0.55 mmol) in EtOH (2 mL) was added all at once. The reaction was stirred at 0° C. for 45 min, after which the solvent was decanted into a separate flask and concentrated to give a white solid. The solid was slurried in $CHCl_3$, filtered, and concentrated to furnish pure sulfoximine (3) as a colorless oil (72 mg, 44 percent). $^1H$ NMR (300 MHz, $CDCl_3$) δ (1.5:1 mixture of diastereomers) 8.8 (s, 2H), 8.0 (d, 2H), 7.8 (d, 2H), 4.7 (q, 1H), 4.6 (q, 1H), 4.0-3.4 (m, s, 4H), 3.0-2.4 (m, 8 H); LC-MS (ELSD): mass calcd for $C_{11}H_{11}F_3N_3OS$ $[M+H]^+$ 290.06. Found 289.99.

EXAMPLE III

Preparation of (1-{6-[chloro(difluoro)methyl]pyridin-3-yl}ethyl)(methyl)-oxido-$\lambda^4$-sulfanylidenecyanamide (4)

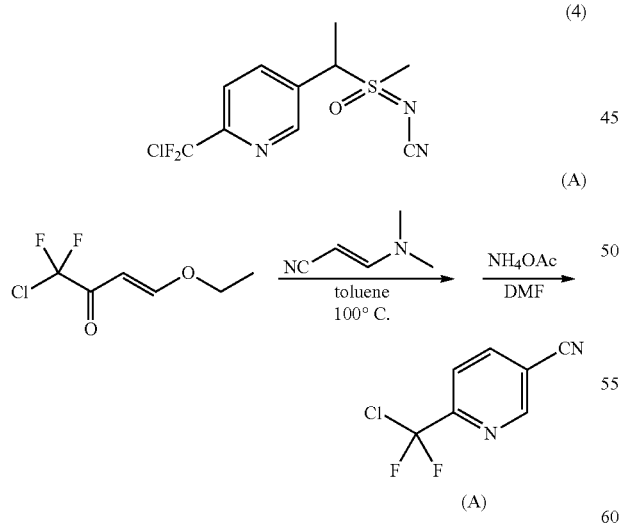

(3E)-1-Chloro-4-ethoxy-1,1-difluorobut-3-en-2-one (7.36 g, 40 mmol) was dissolved in dry toluene (40 mL) and treated with 3-dimethylaminoacrylonitrile (4.61 g, 48 mmol) at room temperature. The solution was heated at 100° C. for 3.5 hr. The solvent was then removed under reduced pressure and the remaining mixture was re-dissolved in DMF (20 mL), treated with ammonium acetate (4.62 g, 60 mmol) and stirred at room temperature overnight. Water was added to the reaction mixture and the resulting mixture was extracted with ether-$CH_2CH_2$ (1:2, v/v) twice. The combined organic layer was washed with brine, dried, filtered and concentrated. The residue was purified on silica gel to give 3.1 g of 6-[chloro(difluoro)methyl]nicotinonitrile (A) as light colored oil in 41 percent yield. GC-MS: mass calcd for $C_7H_3ClF_2N_2$ $[M]^+$ 188. Found 188.

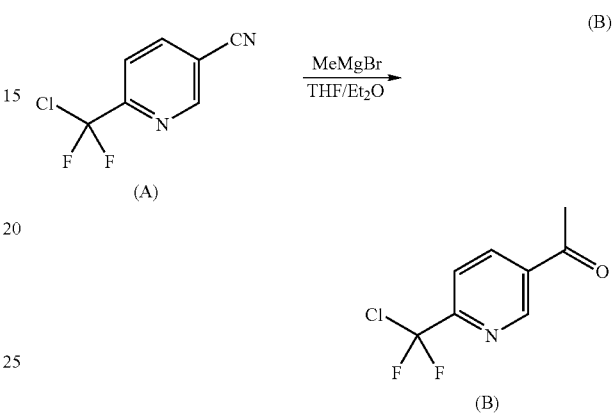

6-[chloro(difluoro)methyl]nicotinonitrile (A) (3.0 g 15.8 mmol) was dissolved in anhydrous ether (25 mL) and cooled in an ice-water bath. A solution of 3 M of methylmagnesium bromide in hexane (6.4 mL, 19 mmol) was added through a syringe. After the addition was over, the mixture was stirred at 0° C. for 5 hr and then at room temperature for 10 hr. The reaction was quenched slowly with 1 N citric acid aqueous solution at 0° C. and the resulting mixture was stirred at room temperature for 1 hr. The pH was adjusted back to pH 7 with saturated $NaHCO_3$ aqueous solution. The two phases were separated and the aqueous phase was extracted with ethyl acetate twice. The combined organic layer was washed with brine, dried over anhydrous $Na_2SO_4$, filtered, and concentrated. The remaining mixture was purified on silica gel eluted with 15 percent acetone in hexane to give 0.88 g of the desired product 1-{6-[chloro(difluoro)methyl]pyridin-3-yl}-ethanone (B) as brownish oil in 30 percent yield. GC-MS: mass calcd for $C_8H_6ClF_2NO$ $[M]^+$ 205. Found 205.

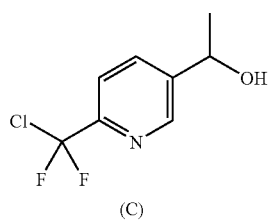

To a solution of 1-{6-[chloro(difluoro)methyl]pyridin-3-yl}ethanone (B) (0.85 g, 4.14 mmol) in MeOH (10 mL) at 0° C. was added NaBH$_4$ (0.16 g, 4.14 mmol). The mixture was stirred for 30 min and 2 M HCl aqueous solution was added until pH reached 7. Solvent was removed under reduced pressure and the remaining mixture was extracted with CH$_2$Cl$_2$ (2×50 mL). The combined organic layer was dried over anhydrous Na$_2$SO$_4$, filtered, concentrated, and dried in vacuo to give 0.798 g of analytically pure 1-{6-[chloro(difluoro)methyl]-pyridin-3-yl}ethanol (C) on GC-MS as a light yellow oil in 93 percent yield. GC–MS: mass calcd for C$_8$H$_6$ClF$_2$NO [M]$^+$ 207. Found 207.

ring in one portion at 0° C. After 10 min, the mixture was allowed to warm to room temperature and stirred overnight. The solvent ethanol was then removed under reduced pressure and the residue was re-taken into ether/CH$_2$Cl$_2$ and brine. The two phases were separated and the organic layer was extracted with CH$_2$Cl$_2$ one more time. The combined organic layer was dried over anhydrous Na$_2$SO$_4$, filtered, concentrated, purified on silica gel using 5 percent ethyl acetate in hexane to give 0.348 g of the 2-[chloro(difluoro)methyl]-5-[1-(methylthio)ethyl]pyridine (E) in 40 percent yield GC-MS: mass calcd for C$_9$H$_{10}$ClF$_2$NS [M]$^+$ 237. Found 237.

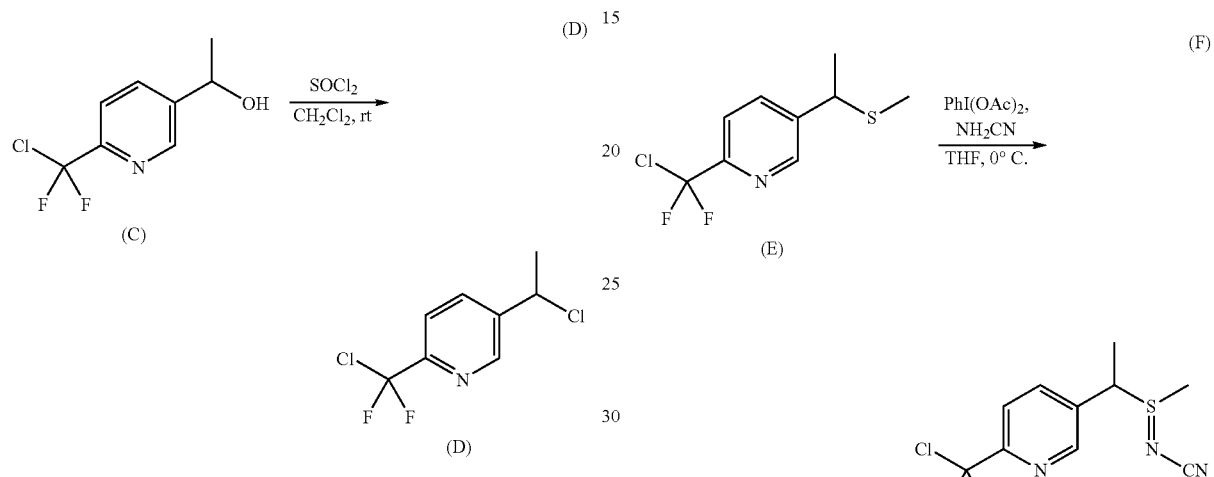

To a solution of 1-{6-[chloro(difluoro)methyl]-pyridin-3-yl}ethanol (0.78 g, 3.77 mmol) in CH$_2$Cl$_2$ (40 mL) was added thionyl chloride (0.54 mL, 7.54 mmol) dropwise at room temperature. After 1 hr, the reaction was quenched slowly with saturated NaHCO$_3$ aqueous solution and the two phases were separated. The organic layer was dried over Na$_2$SO$_4$, filtered, concentrated, and dried in vacuum to give 0.83 g of the crude 2-[chloro(difluoro)methyl]-5-(1-chloroethyl)pyridine (D) as brown oil in 98 percent yield, which was directly used for the next step reaction. GC-MS: mass calcd for C$_8$H$_7$Cl$_2$F$_2$N [M]$^+$ 225. Found 225.

To a stirred solution of 2-[chloro(difluoro)methyl]-5-[1-(methylthio)-ethyl]pyridine (E) (0.32 g, 1.35 mmol) and cyanamide (0.058 g, 1.35 mmol) in THF (7 mL) was added iodobenzene diacetate (0.44 g, 1.35 mmol) in one portion at 0° C. and the resulting mixture was stirred at this temperature for 1 hr and then at room temperature for 2 hr. The solvent was then removed under reduced pressure and the resulting mixture was dissolved in CH$_2$Cl$_2$, washed with half-saturated brine, dried over anhydrous Na$_2$SO$_4$, filtered, concentrated, and purified on silica gel using 50 percent acetone in hexane to give 0.175 g of (1-{6-[chloro-(difluoro)methyl]pyridin-3-yl}ethyl)(methyl)-λ$^4$-sulfanylidenecyanamide (F) as light-yellow oil in 48 percent yield. $^1$H NMR (300 MHz, CDCl$_3$) δ 8.71 (d, J=1.8 Hz, 1H), 7.91 (dd, J=8.4, 1.8 Hz, 1H) 7.78 (d, J=8.4 Hz, 1H), 4.42 (q, J=6.9 Hz, 1H), 2.64 (s, 3H), 1.92 (d, J=6.9 Hz, 3H); LC-MS: mass calcd for C$_H$H$_{10}$ClF$_2$N$_3$S [M+1]$^+$ 278. Found 278.

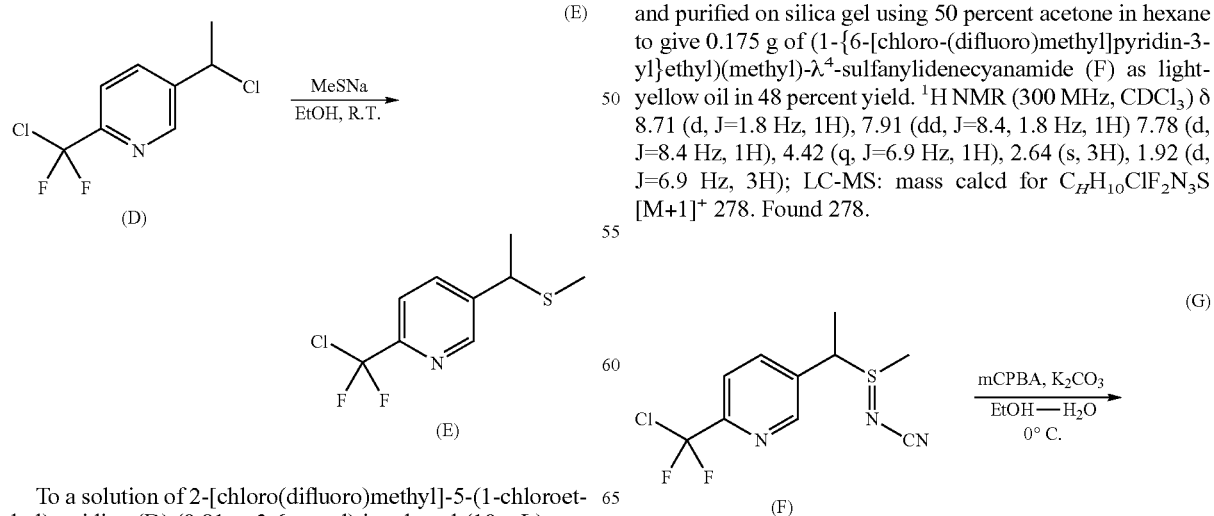

To a solution of 2-[chloro(difluoro)methyl]-5-(1-chloroethyl)pyridine (D) (0.81 g, 3.6 mmol) in ethanol (10 mL) was added sodium thiomethoxide (0.52 g, 7.4 mmol) under stir- -continued

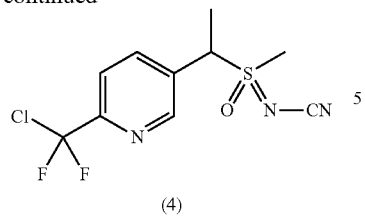

(4)

To a stirred solution of (1-{6-[chloro(difluoro)methyl]pyridin-3-yl}ethyl)-(methyl)-λ⁴-sulfanylidenecyanamide (F) (0.16 g, 0.6 mmol) in ethanol (10 mL) was added 20 percent potassium carbonate aqueous solution (1.24 g, 1.8 mmol) at 0° C. under stirring. After 10 min stirring, 80 percent mCPBA (0.19 g, ca 0.9 mmol) was added to the mixture, which was stirred at 0° C. for 2 hr after which the reaction was quenched with a spatula of solid sodium thiosulfate. Most of the solvent ethanol was removed under reduced pressure and an aqueous saturated NaHCO₃-brine (1:1, v/v) solution was added and the mixture extracted with chloroform three times. The combined organic layer was dried over Na₂SO₄, filtered and concentrated. The residue was purified on silica gel using 35-50 percent acetone in hexane as eluent to give 0.092 g of the product (1-{6-[chloro(difluoro)-methyl]pyridin-3-yl}ethyl)(methyl)oxido-λ⁴-sulfanylidenecyanamide (4) as colorless oil in 57 percent yield. ¹H NMR (300 MHz, CDCl₃) δ 8.79 (s, 1H), 8.09 (d, J=8.1 Hz, 1H), 7.80 (d, J=8.1 Hz, 1H), 4.73 (q, J=7.2 Hz, 1H), 3.16 and 3.11 (2 s, 3H, a mixture of two diastereomeric α-CH3 groups between the sulfoximine and the pyridine tail), 2.00 (d, J=7.2 Hz, 3H); LC-MS: mass calcd for C₁₀H₁₀ClF₂N₃OS [M-I]⁺ 292. Found 292.

EXAMPLE IV

Preparation of [1-(6-trichloromethylpyridin-3-yl)ethyl](methyl)-oxido-λ⁴-sulfanylidenecyanamide (5)

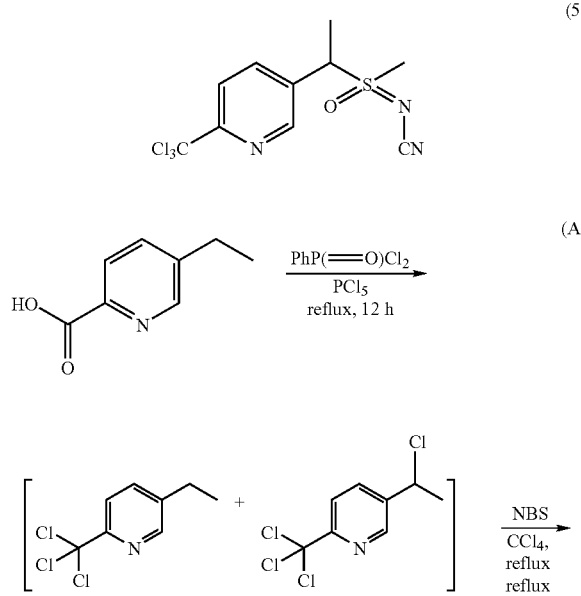

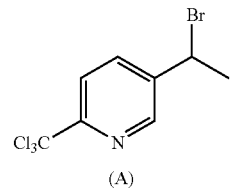

(A)

A mixture of 5-ethylpyridine-2-carboxylic acid (1.98 g, 13 mmol), phenyl-phosphonic dichloride (2.8 g, 14.3 mmol), phosphorus pentachloride (7.7 g, 32 mmol) was stirred and slowly heated. Once a clear yellow liquid was formed, the mixture was heated to reflux overnight. After cooling, the volatiles were removed under reduced pressure. The residue was carefully poured into saturated sodium carbonate aqueous solution cooled in an ice-water bath. The aqueous phase was then extracted with CH₂Cl₂ two times. The combined organic layer was washed with brine, dried over anhydrous Na₂SO₄, filtered, concentrated, and partially purified on silica gel eluted with 10 percent EtOAc in hexane to give 2.7 g of crude product containing both 5-ethyl-2-(trichloromethyl)pyridine and 5-(1-chloro-ethyl)-2-(trichloromethyl)pyridine in an approximate 3:1 ratio (GC data, masses calcd for C₈H₈Cl₃N and C₈H₇Cl₄N [M]⁺ 223 and 257 respectively. Found 223 and 257 respectively).

A mixture of the above-mentioned crude product (2.6 g) in carbon tetrachloride (100 mL) was then treated with 80 percent of N-bromosuccinimide (1.9 g, 11 mmol) and benzoylperoxide (0.66 g, 0.275 mmol) and then refluxed overnight. The solid was filtered off, the filtrate concentrated and the resulting residue purified on silica gel using 4 percent EtOAc in hexane to give 1.0 g of the desired product 5-(1-bromoethyl)-2-(trichloromethyl)pyridine (A) as a yellow solid. The combined yield for the two steps was 25 percent. GC-MS: mass calcd for C₈H₇BrCl₃N [M-I—Cl]⁺ 266. Found 266.

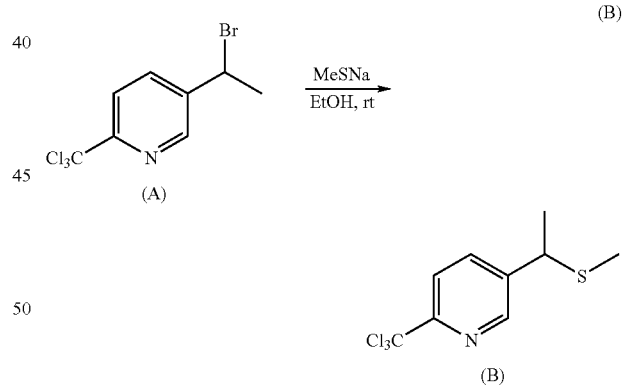

A solution of 5-(1-bromoethyl)-2-(trichloromethyl)pyridine (A) (0.95 g, 3.14 mmol) in ethanol (15 mL) was treated with sodium thiomethoxide (0.44 g, 6.29 mmol) portionwise at 0° C. The mixture was stirred at room temperature overnight. The solvent ethanol was then removed under a reduced pressure and the residue was re-taken into CH₂Cl₂ and brine. The two phases were separated and the organic layer was dried over anhydrous Na₂SO₄, filtered, concentrated. The residue was purified on silica gel using 5 percent EtOAc in hexane to give 0.57 g of the partially pure 5-[1-(methylthio)ethyl]-2-(trichloromethyl)pyridine (B) in 67 percent crude yield. GC-MS: mass calcd for C₉H₁₀Cl₃NS [M]⁺ 269. Found 269.

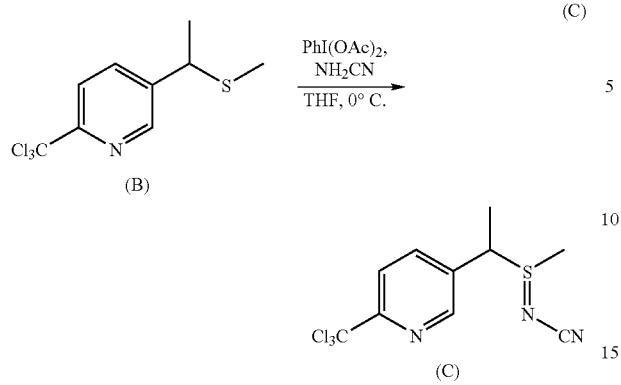

To a stirred solution of 5-[1-(methylthio)ethyl]-2-(trichloromethyl)-pyridine (B) (0.55 g 2.3 mmol) and cyanamide (0.097 g, 2.3 mmol) in THF (7 mL) cooled to 0° C. was added iodobenzene diacetate (0.75 g, 2.3 mmol) in one portion. The resulting mixture was stirred at 0° C. for 1 hr and then at room temperature for 2 hr. The solvent was removed in vacuo and the resulting mixture was purified on silica gel using 50 percent acetone in hexane to give 0.254 g of (1E)-methyl{1-[6-(trichloromethyl)pyridin-3-yl]ethyl}-λ⁴-sulfanylidenecyanamide (C) as an off-white solid in 40 percent yield. ¹H NMR for the diastereomeric mixture (300 MHz, d₆-acetone) δ 8.87 (s, 1H), 8.21-8.25 (m, 2H), 4.65-4.76 (m, 1H), 2.86-2.66 (m, 3H), 1.88-1.92 (m, 3H).

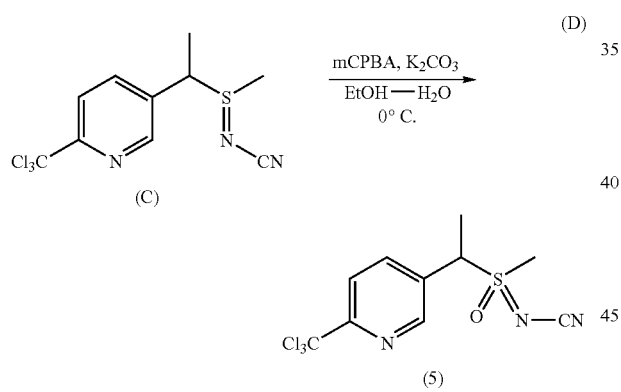

To a stirred solution of (1E)-methyl{1-[6-(trichloromethyl)pyridin-3-yl]ethyl}-λ⁴-sulfanylidenecyanamide (C) (0.20 g, 0.65 mmol) in ethanol (15 mL) was added 20 percent aqueous potassium carbonate solution (1.3 mL) at 0° C., followed by addition of 80 percent mCPBA. The resulting mixture was stirred for 2 hr at 0° C. and then quenched with solid sodium thiosulfate. Most of the solvent was evaporated and 1:1 aqueous saturated NaHCO₃-brine (v/v) was added and the mixture was extracted with chloroform three times. The combined organic layer was dried over anhydrous Na₂SO₄, filtered and concentrated. The residue was purified on silica gel using 40 percent acetone in hexane to give 0.10 g of [1-(6-trichloromethylpyridin-3-yl)ethyl](methyl)-oxido-λ⁴-sulfanylidene-cyanamide (5) as colorless oil in 50 percent yield. ¹H NMR (300 MHz, CDCl₃) δ 8.83 (s, 1H), 8.12-8.23 (m, 1H), 5.15 (q, 1H), 3.37 and 3.28 (2 s, 3H, a mixture of two diastereomeric α-CH3 groups between the sulfoximine and the pyridine tail), 2.03 (d, 3H); LC-MS: mass calcd for C₁₀H₁₂Cl₃N₃OS [M+1] 328. Found 328.

EXAMPLE V

Preparation of [1-(6-difluoromethylpyridin-3-yl) ethyl](methyl)-oxido-λ⁴-sulfa-nylidenecyanamide (6)

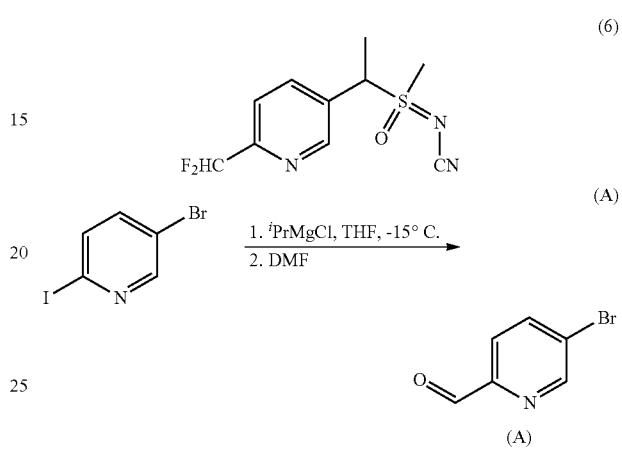

To a solution of 2-iodo-5-bromopyridine (18.4 g, 65 mmol) in THF (100 mL) at −15° C. was added isopropylmagnesium chloride (2M, 35 mL, 70 mmol) dropwise at a rate such that the temperature of the reaction did not exceed 0° C. The reaction was stirred at −15° C. for 1 h, then DMF (7.5 mL, 97 mmol) was added dropwise at a rate such that the temperature of the reaction did not exceed 0° C. The reaction was stirred for 30 min, then warmed to room temperature for an additional 1 h. The reaction was cooled back down to 0° C. and 2 N HCl (80 mL) was added dropwise, maintaining the temperature below 20° C. After stirring for 30 min, 2 N NaOH was added until pH 7 was reached. The organic layer was then separated and the aqueous layer extracted with CH₂Cl₂ (3×). The combined organic layers were dried over MgSO₄, concentrated and purified by flash chromatography (SiO₂, 10% EtOAc/hexanes) to furnish 5-bromopyridine-2-carbaldehyde (A) as a white solid (7.3 g, 60 percent). ¹H NMR (300 MHz, CDCl₃) δ 10.0 (s, 1H), 8.9 (s, 1H), 8.0 (d, 1H), 7.8 (d, 1H).

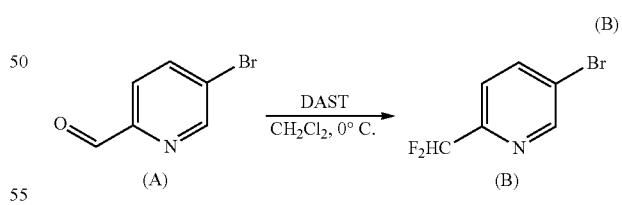

To a cooled solution of 5-bromopyridine-2-carbaldehyde (A) (7.0 g, 38 mmol) in CH₂Cl₂ (300 mL) at −78° C. was added diethylaminosulfur trifluoride (DAST, 10.8 mL, 83 mmol). The reaction was allowed to warm to room temperature over the course of 6 h, then it was quenched slowly with H₂O, washed with saturated aqueous NaHCO₃ and dried over Na₂SO₄. Concentration and purification by silica gel plug (CH₂Cl₂ eluent) furnished 5-bromo-2-difluoromethylpyridine (B) as brown crystals (5.3 g, 67 percent). ¹H NMR (300 MHz, CDCl₃) δ 8.8 (s, 1H), 8.0 (d, 1H), 7.6 (d, 1H), 6.6 (t, 1H).

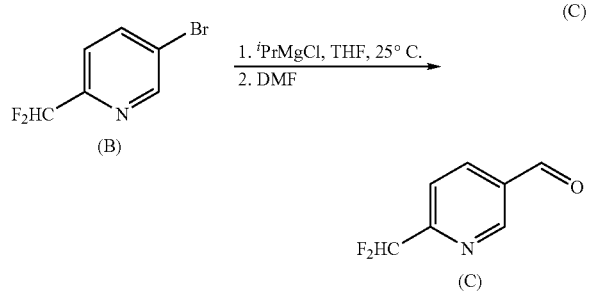

To a solution of 5-bromo-2-difluoromethylpyridine (B) (1.8 g, 8.6 mmol) in THF (40 mL) at 25° C. was added isopropylmagnesium chloride (2M, 8.6 mL, 17 mmol) dropwise. The reaction was allowed to stir for 2 h, then DMF (660 μL, 8.6 mmol) was added and the reaction was stirred for an additional 22 h. The reaction was quenched with 2M HCl and basified with 1M NaOH until pH 7 reached. The organic layer was separated and the aqueous layer was extracted with CH$_2$Cl$_2$. The combined organic layers were dried over Na$_2$SO$_4$, concentrated and purified by flash chromatography (10 percent EtOAc/hexanes) to furnish 6-difluoromethylpyridine-3-carbaldehyde (C) as an orange oil (320 mg, 24 percent).

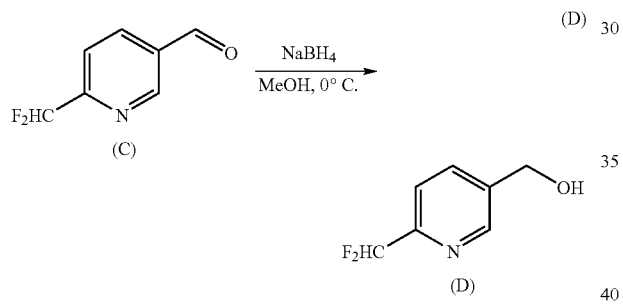

To a solution of 6-difluoromethylpyridine-3-carbaldehyde (C) (500 mg, 3.2 mmol) in MeOH (10 mL) at 0° C. was added NaBH$_4$ (60 mg, 1.6 mmol). The reaction was allowed to stir for 30 min, then 2M HCl was added until pH 2 was reached. The resulting solution was extracted with CH$_2$Cl$_2$ (3×) and the combined organic layers dried over Na$_2$SO$_4$ and concentrated to furnish (6-difluoromethyl-pyridin-3-yl)methanol (D) as an orange oil (420 mg, 82 percent) which was used in the next step without further purification. $^1$H NMR (300 MHz, CDCl$_3$) δ 8.6 (s, 1H), 7.9 (d, 1H), 7.6 (d, 1H), 6.6 (t, 1H), 4.8 (s, 2H).

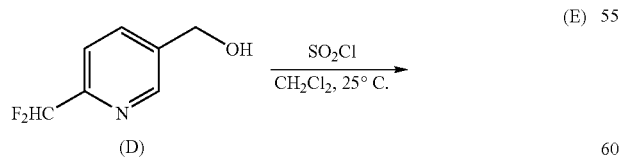

To a solution of (6-difluoromethylpyridin-3-yl)methanol (D) (450 mg, 2.8 mmol) in CH$_2$Cl$_2$ (10 mL) at room temperature was SO$_2$Cl (230 μL, 3.1 mmol). The reaction was allowed to stir for 1 h, then the reaction was quenched slowly with saturated aqueous NaHCO$_3$. The aqueous phase was extracted with CH$_2$Cl$_2$ (3×) and the combined organic layers were dried over Na$_2$SO$_4$ and concentrated. The resulting solution was extracted with CH$_2$Cl$_2$ (3×) and the combined organic layers dried over Na$_2$SO$_4$ and concentrated to furnish 5-chloromethyl-2-difluoromethylpyridine (E) as a reddish brown oil (490 mg, 98%) which was used in the next step without further purification. $^1$H NMR (300 MHz, CDCl$_3$) δ 8.7 (s, 1H), 7.9 (d, 1H), 7.6 (d, 1H), 6.6 (t, 1H), 4.6 (s, 2H).

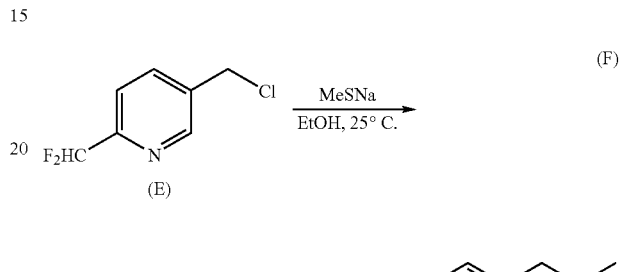

To a solution of sodium thiomethoxide (240 mg, 3.3 mmol) in EtOH (10 ml) at room temperature was added a solution of 5-chloromethyl-2-difluoromethylpyridine (E) (490 mg, 2.8 mmol) in EtOH (3 mL). The reaction was allowed to stir for 9 h, then the reaction was concentrated, taken up in Et$_2$O, and washed with H$_2$O. The organic phase was dried over Na$_2$SO$_4$ and concentrated to furnish 2-difluoromethyl-5-methylthiomethyl-pyridine (F) as an orange oil (422 mg, 81%) which was used in the next step without further purification. $^1$H NMR (300 MHz, CDCl$_3$) δ 8.6 (s, 1H), 7.8 (d, 1H), 7.6 (d, 1H), 6.6 (t, 1H), 3.7 (s, 2H), 2.0 (s, 3H).

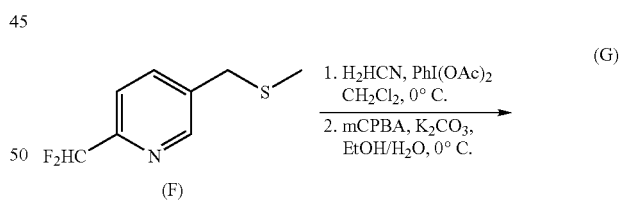

[(6-Difluoromethylpyridin-3-yl)methyl](methyl)-oxido-λ$^4$-sulfanylidenecyanamide (G) was synthesized from 2-difluoromethyl-5-methylthiomethylpyridine (F) in two steps as described in Examples I-B and I-C. Isolated as a white solid (51% yield). $^1$H NMR (300 MHz, CDCl$_3$) δ 8.7 (s, 1H), 8.0 (d, 1H), 7.8 (d, 1H), 6.7 (t, 1H), 4.7 (dd, 2H), 3.2 (s, 3H); LC-MS (ELSD): mass calcd for C$_9$H$_{10}$F$_2$N$_3$OS [M+H]$^+$, 246. Found 246.

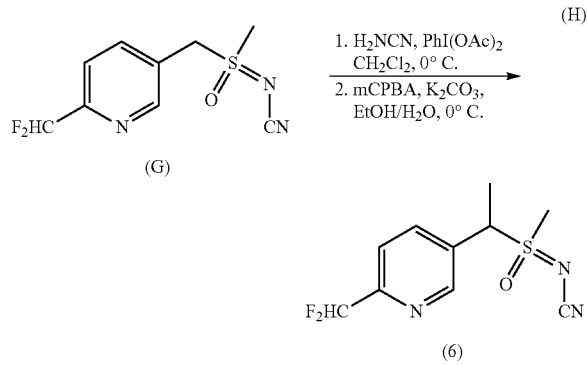

[1-(6-difluoromethylpyridin-3-yl)ethyl](methyl)-oxido-λ⁴-sulfanylidenecyanamide (6) was synthesized from [(6-difluoromethylpyridin-3-yl)methyl](methyl)-oxido-λ⁴-sulfan-ylidenecyanamide (G) in one step as described in Example I. Isolated as a colorless oil (74 percent yield) and a 1:1 mixture of diastereomers. $^1$H NMR (300 MHz, CDCl$_3$) δ (mixture of two diastereomers) 8.7 (s, 2H), 8.0 (d, 2H), 7.8 (d, 2H), 6.7 (t, 2H), 4.6 (q, 2H), 3.1 (s, 3H), 3.0 (s, 3H), 2.0 (d, 6H), LC-MS (ELSD): mass calcd for C$_{10}$H$_{12}$F$_2$N$_3$OS [M+H]$^+$, 260. Found 260.

EXAMPLE VI

Preparation of [1-(6-pentafluoroethylpyridin-3-yl)ethyl]methyl)-oxido-λ⁴-sulfanylidenecyanamide (7)

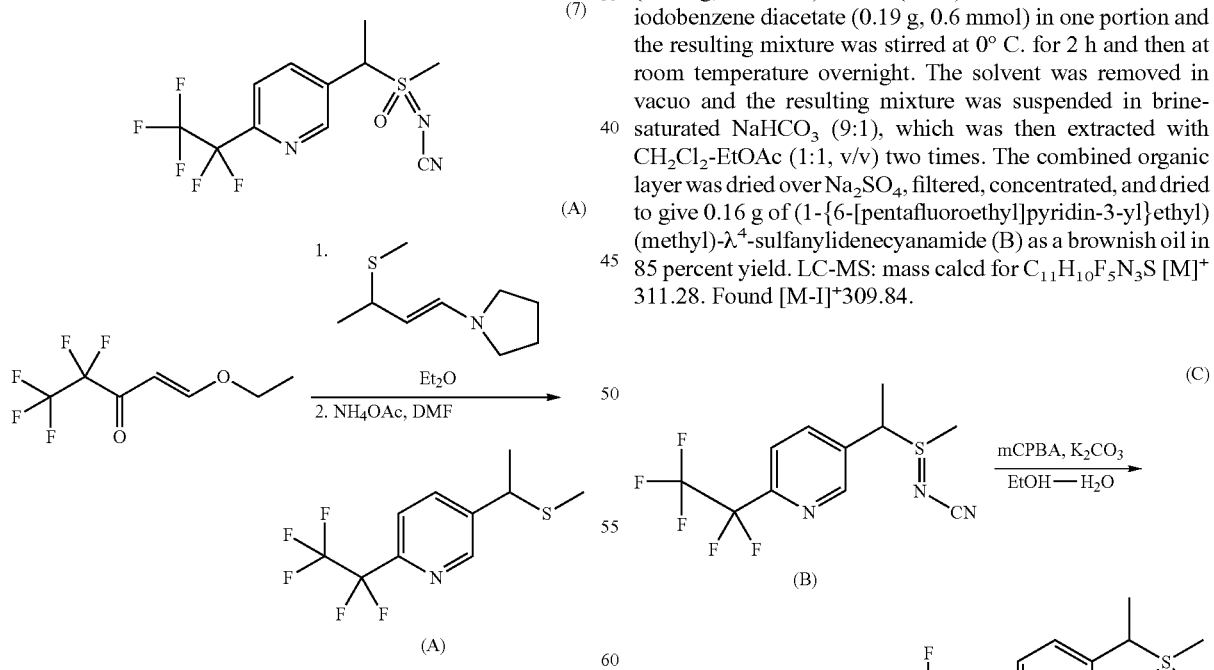

(E)-1-Ethoxy-4,4,5,5,5-pentafluoropent-1-en-3-one (1.09 g, 5 mmol) in anhydrous ethyl ether (5 mL) was treated with 1-((E)-3-methylthiobut-1-enyl)pyrrolidine (0.85 g, 5 mmol) in 2 mL dry ether at −15° C. over a period of 5 min and the reaction was continued for 20 min. Then the temperature was allowed to rise to room temperature and the reaction continued for 3 h. The solvent was removed under reduced pressure and the residue re-dissolved in anhydrous DMF (5 mL). Ammonium acetate (0.58 g, 7.5 mmol) was added and the mixture stirred at room temperature over a weekend. Water was added and mixture extracted with ether three times. The combined organic layer was washed with brine, dried over anhydrous Na$_2$SO$_4$, filtered, concentrated, and purified on silica gel eluted with 8% EtOAc in hexane (v/v) to give 0.16 g of the desired 5-(1-methylthioethyl)-2-pentafluoroethylpyridine (A) as brownish colored oil in 12 percent yield. GC-MS: mass calcd for C$_{10}$H$_{11}$F$_2$N$_3$S [M]$^+$ 271. Found 271.

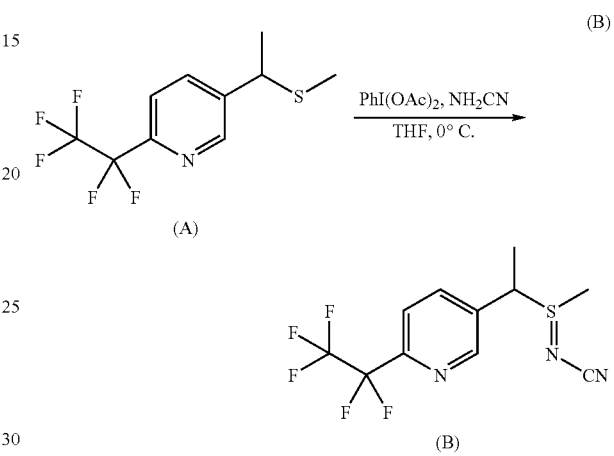

To a stirred solution of the 5-(1-methylthioethyl)-2-pentafluoro-ethylpyridine (A) (0.16 g, 0.6 mmol) and cyanamide (0.025 g, 0.6 mmol) in THF (3 mL) cooled to 0° C. was added iodobenzene diacetate (0.19 g, 0.6 mmol) in one portion and the resulting mixture was stirred at 0° C. for 2 h and then at room temperature overnight. The solvent was removed in vacuo and the resulting mixture was suspended in brine-saturated NaHCO$_3$ (9:1), which was then extracted with CH$_2$Cl$_2$-EtOAc (1:1, v/v) two times. The combined organic layer was dried over Na$_2$SO$_4$, filtered, concentrated, and dried to give 0.16 g of (1-{6-[pentafluoroethyl]pyridin-3-yl}ethyl)(methyl)-λ⁴-sulfanylidenecyanamide (B) as a brownish oil in 85 percent yield. LC-MS: mass calcd for C$_{11}$H$_{10}$F$_5$N$_3$S [M]$^+$ 311.28. Found [M-I]$^+$309.84.

To a stirred solution of the 80 percent 3-chloroperoxybenzoic acid (0.17 g, ca 0.8 mmol) in ethanol (3 mL) cooled to 0° C. was added 20 percent aqueous potassium carbonate (1.0 mL, 1.5 mmol) and the resulting mixture was stirred at 0° C. for 20 min. Then (1-{(6[pentafluoro-ethyl]pyridin-3-yl}ethyl)(methyl)-$\lambda^4$-sulfanylidenecyanamide (B) was added at once and the mixture was stirred at 0° C. for 1 h. The reaction was quenched with a small spatula of solid sodium thiosulfate. Most of the solvent was evaporated and brine solution was added and the mixture extracted with $CH_2Cl_2$ three times. The combined organic layer was dried over $Na_2SO_4$, filtered and concentrated and the residue was purified on silica gel using 10% acetone in $CH_2Cl_2$ (v/v) to give 0.089 g of [1-(6-pentalluoroethylpyridin-3-yl)ethyl](methyl)-oxido-$\lambda^4$-sulfanylidenecyanamide (7) as a white solid in 54% yield. LC-MS: mass calcd for $C_{10}H_{10}F_5N_3OS$ $[M]^+$ 327.28. Found $[M-1]^+$ 325.83.

EXAMPLE VII

Preparation of 2-trifluoromethyl-5-(1-{methyl (oxido)[oxido(oxo)hydrazono]-$\lambda^4$-sulfanyl}ethyl) pyridine (8)

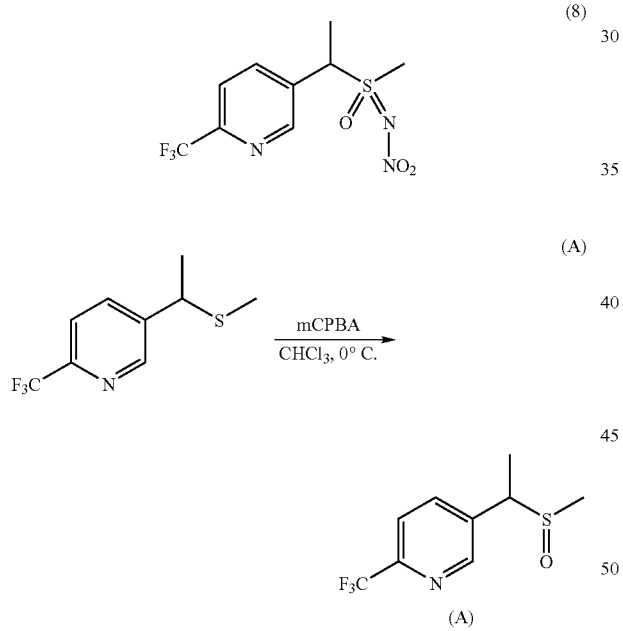

To a solution of 5-(1-methylthioethyl)-2-trifluoromethylpyridine (2.0 g, 9 mmol) in $CHCl_3$ (20 mL) at 0° C. was added solution of mCPBA (2.1 g, 10 mmol) in $CHCl_3$ (25 mL) over the course of 1.5 h. The solution was stirred an additional 2 h, then it was concentrated and purified by flash chromatography (10 percent $MeOH/CH_2Cl_2$) to furnish 5-(1-methylsulfinyl-ethyl)-2-trifluoromethylpyridine (A) as a yellow oil (710 mg, 33 percent) and a ~2:1 mixture of diastereomers. $^1$H NMR (300 MHz, $CDCl_3$) δ (major diastereomer) 8.7 (s, 1H), 7.8 (d, 1H), 7.7 (d, 1H), 4.0 (q, 1H), 2.4 (s, 3H), 1.75 (d, 3H); (minor diastereomer) 8.6 (s, 1H), 7.9 (d, 1H), 7.7 (d, 1H), 3.8 (q, 1H), 2.3 (s, 3H), 1.8 (d, 3H); LC-MS (ELSD): mass calcd for $C_9H_{11}F_3NOS$ $[M+H]^+$, 238. Found 238.

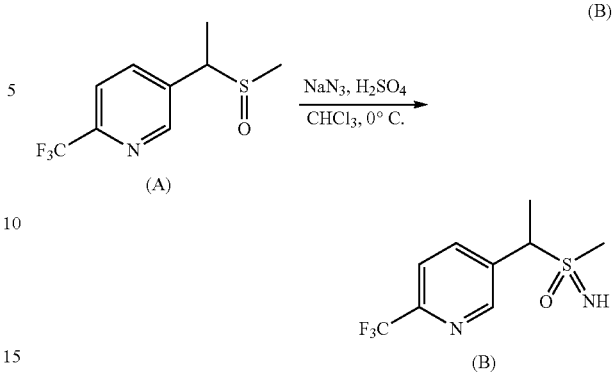

To a solution of 5-(1-methylsulfinylethyl)-2-trifluoromethylpyridine (A) (600 mg, 2.5 mmol) in $CHCl_3$ (5 mL) at 0° C. was added sodium azide (260 mg, 4.0 mmol) and $H_2SO_4$ (1 mL). The reaction was warmed to 55° C. until gas evolution was observed, then it was cooled back down to room temperature overnight. The liquid was decanted into a separate flask and the residual syrup was dissolved in $H_2O$, basified with $Na_2CO_3$ and extracted with $CH_2Cl_2$. The combined organic layers were dried over $Na_2SO_4$, concentrated and purified by flash chromatography to furnish 5-[1-(methylsulfonimidoyl)ethyl]-2-trifluoromethylpyridine (B) as a yellow oil (130 mg, 20 percent) and a —1:1 mixture of diastereomers. $^1$H NMR (300 MHz, $CDCl_3$) δ (mixture of diastereomer) 8.8 (d, 2H), 8.0 (dd, 2H), 7.8 (d, 2H), 4.4 (m, 2H), 2.9 (s, 3H), 2.85 (s, 3H), 1.8 (m, 6H); LC-MS (ELSD): mass calcd for $C_9H_{11}F_3N_2OS$ $[M]^+$, 252. Found 252.

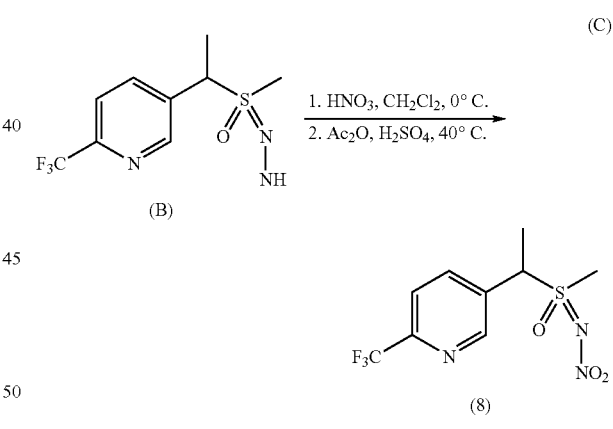

To a solution of 5-[1-(methylsulfonimidoyl)ethyl]-2-trifluoromethylpyridine (B) (100 mg, 0.4 mmol) in $CH_2Cl_2$ (2 mL) at 0° C. was added $HNO_3$ (16 μl, 0.4 mmol) dropwise. To the resulting suspension was added acetic anhydride (750 μL) and concentrated $H_2SO_4$ (5 μL) and the mixture was heated to 40° C. The suspension slowly became homogeneous over the course of 15 min. The solvent was then removed and the crude residue was dissolved in $H_2O$. Solid $Na_2CO_3$ was added until pH 8 was reached and the aqueous phase was extracted with $CH_2Cl_2$. The combined organic layers were dried over $Na_2SO_4$, concentrated and purified by flash chromatography to furnish 2-trifluoromethyl-5-(1-{methyl(oxido)-[oxido (oxo)hydrazono]-$\lambda^4$-sulfanyl}pyridine (8) as a yellow oil (22 mg, 19 percent) and a 1:1 mixture of diastereomers. $^1$H NMR (300 MHz, $CDCl_3$) δ (mixture of diastereomers) 8.8 (d, 2H), 8.1 (m, 2H), 7.8 (m, 2H), 5.1 (q, 1H), 5.0 (q, 1H), 3.3 (s, 3H), 3.25 (s, 3H), 2.0 (m, 6H); LC-MS (ELSD): mass calcd for $C_9H_{11}F_3N_3O_3S$ [M+H]$^+$, 298. Found 298.

EXAMPLE VIII

Preparation of [6-(1,1-difluoroethyl)pyridin-3-yl) ethyl](methyl)-oxido-$\lambda^4$-sulfanylidenecyanamide (9)

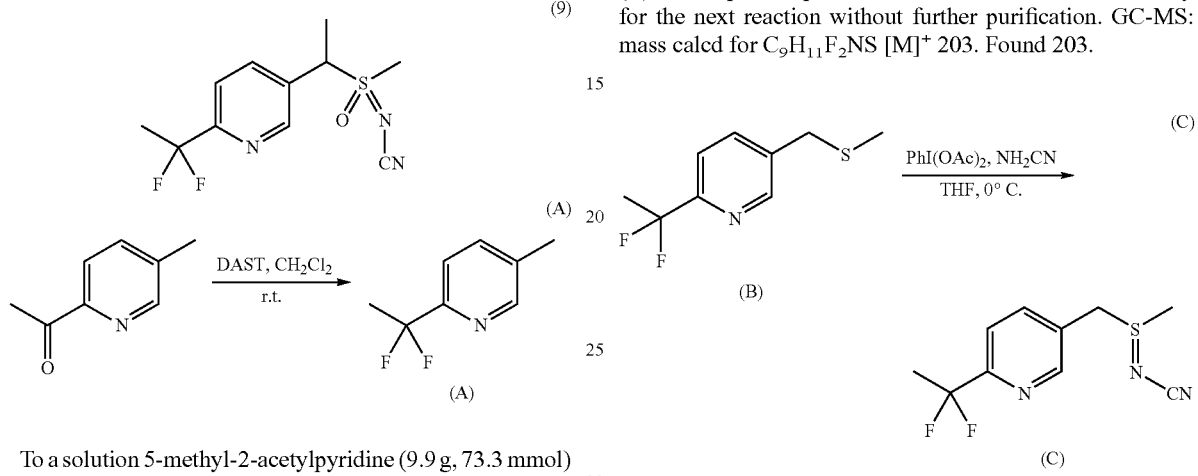

To a solution 5-methyl-2-acetylpyridine (9.9 g, 73.3 mmol) in molecule sieves-dried $CH_2Cl_2$ (150 mL) was added diethylamino sulfolnyltrifluoride (DAST) (25.8 g, 260 mmol) at room temperature and the mixture was stirred at room temperature overnight. More DAST (12 g, 74 mmol) was added and the reaction continued for two more days after which an additional DAST (3.8 g, 23 mmol) was added and the reaction continued for another 3 days. After the reaction was quenched slowly with saturated $NaHCO_3$ at 0° C., the organic phase was separated, dried over $Na_2SO_4$, filtered, and concentrated. The residue was purified on silica gel eluted with 8% EtOAc in hexane to give 3.91 g of 2-(1,1-difluoroethyl)-5-methylpyridine (A) as a light brownish oil in 34 percent yield. GC-MS: mass calcd for $C_8H_9F_2N$ [M]$^+$ 157. Found 157.

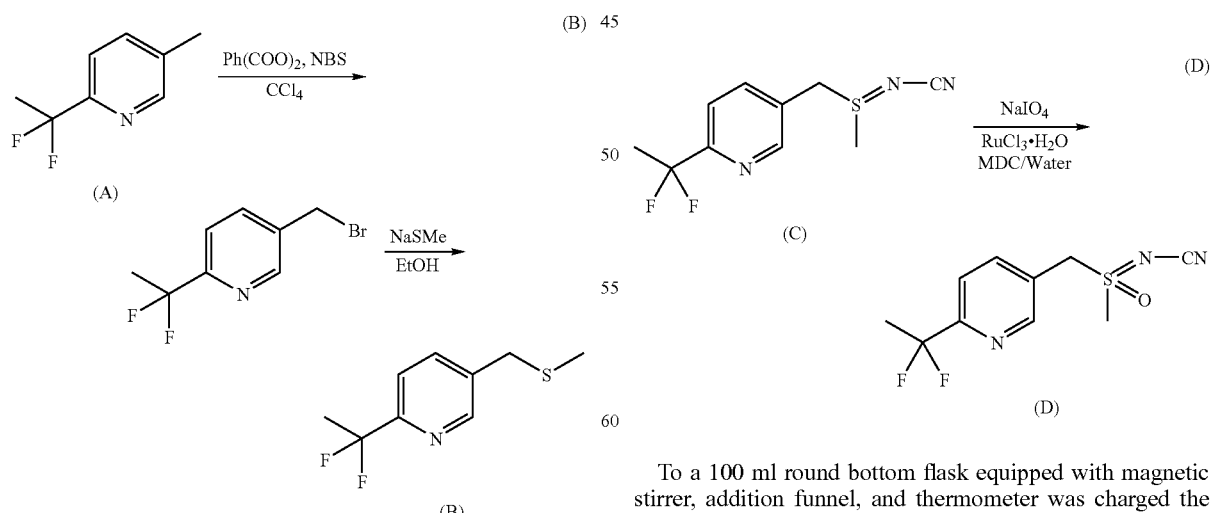

A mixture of 2-(1,1-difluoroethyl)-5-methylpyridine (A) (2.0 g, 12.7 mmol), N-bromosuccinimide (2.2 g, 12.7 mmol) and benzoylperoxide (0.15 g, 0.63 mmol) in carbon tetrachloride (100 mL) was refluxed overnight. After the solid was removed by filtration, the filtrate was concentrated. The residue was re-dissolved in ethanol (40 mL) and sodium thiomethoxide (1.33 g, 19 mmol) was added at room temperature and stirred for 3 h. The solvent was removed under reduced pressure and the remaining mixture was dissolved in $CH_2Cl_2$ and water. After separation, the organic layer was dried over $Na_2SO_4$, filtered and concentrated. The crude product 2-(1,1-difluoroethyl)-5-methylthiomethyl-pyridine (B) was 94 percent pure on GC/MS, which was used directly for the next reaction without further purification. GC-MS: mass calcd for $C_9H_{11}F_2NS$ [M]$^+$ 203. Found 203.

To a stirred solution of 2-(1,1-difluoroethyl)-5-methylthiomethylpyridine (B) (1.22 g. 6.0 mmol) and cyanamide (0.25 g, 6.0 mmol) in THF (7 mL) cooled to 0° C. was added iodobenzene diacetate (1.93 g, 6.0 mmol) in one portion and the resulting mixture was stirred at 0° C. for 1 h and then at room temperature for 2 h. The solvent was removed in vacuo and the resulting mixture was purified on silica gel using 60 percent acetone in hexane (v/v) to give 1.22 g of [(6-(1,1-difluoroethylpyridin-3-yl)methyl](methyl)-$\lambda^4$-sulfanylidenecyanamide (C) (84 percent yield) as brownish oil which turned into a brownish solid after standing in the refrigerator overnight. LC-MS: mass calcd for $C_{10}H_{11}F_2N_3S$ [M]$^+$ 243.28. Found [M+]$^+$ 244.11.

To a 100 ml round bottom flask equipped with magnetic stirrer, addition funnel, and thermometer was charged the sodium periodate (0.95 g, 4.44 mmol) and water (12 mL). After the solid had dissolved, 15 mL of $CH_2Cl_2$ was added followed by the ruthenium trichloride hydrate (0.033 g, 0.15 mmol). [(6-(1,1-difluoroethylpyridin-3-yl)methyl](methyl)-

λ$^4$-sulfanylidenecyanamide (C) (0.72 g, 2.96 mmol) dissolved in 5 mL of CH$_2$Cl$_2$ was added dropwise over a period of 30 min. The mixture was stirred rapidly at room temperature for 1.5 h and then filtered through a filtering paper to remove some insolubles. The mixture was then separated in separation funnel after ethyl acetate was added to facilitate the separation.

The aqueous phase was extracted with CH$_2$Cl$_2$ twice. The combined organics was washed with brine, dried over dry Na$_2$SO$_4$, filtered, concentrated, and briefly purified on silica gel with 70 percent acetone in hexane to give 0.652 g of the desired product [(6-(1,1-difluoroethylpyridin-3-yl)methyl]methyl)-oxido λ$^4$-sulfanylidenecyanamide (D) as a white solid in 87 percent yield. LC-MS: mass calcd for C$_{10}$H$_{11}$F$_2$N$_3$OS [M]$^+$ 259.28. Found [M+1]$^+$ 260.02.

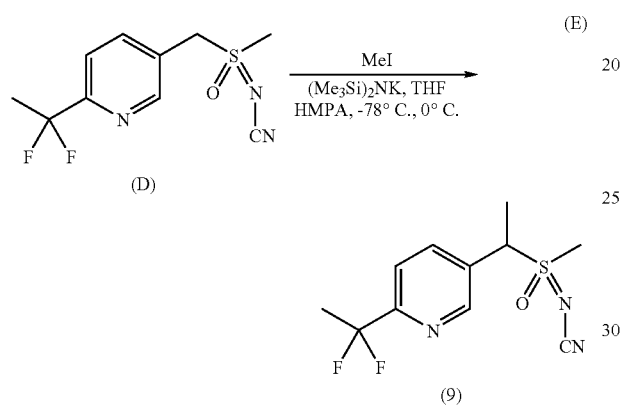

To a solution of [(6-(1,1-difluoroethylpyridin-3-yl)methyl]methyl)-oxido λ$^4$-sulfanylidenecyanamide (D) (0.55 g, 2.0 mmol) and HMPA (0.09 mL, 0.55 mmol) in 20 mL anhydrous THF was added 0.5 M potassium bis(trimethylsilyl) amide in toluene (4.4 mL, 2.2 mmol) at −78° C. dropwise. After 45 min, iodomethane (0.14 mL, 2.2 mmol) was added in one portion via a syringe. Ten minutes later, the temperature was allowed to rise to 0° C. and mixture continued to stir for 1.5 h. The reaction was quenched with saturated aqueous NH$_4$Cl, diluted with brine, extracted once each with EtOAc and CH$_2$Cl$_2$. The combined organic layer was dried over Na$_2$SO$_4$, filtered, and concentrated. The residue was purified by preparative HPLC to give 0.15 g of the desired [6-(1,1-difluoroethyl)pyridin-3-yl]ethyl](methyl)-oxido-λ$^4$-sulfanylidenecyanamide (9) in 26 percent yield. LC-MS: mass calcd for C$_{11}$H$_{23}$F$_2$N$_3$OS [M]$^+$ 273.31. Found [M+1]$^+$ 274.21.

Further details regarding Examples I-VIII and other related compounds are provided in U.S. Patent Application Publication 2007/0203191 A1, the contents of which are incorporated herein by reference in their entirety.

It should be appreciated that the compositions of this invention can include compounds that can exist as one or more stereoisomers. For example, in certain embodiments, the compositions include a mixture of stereoisomers of a compound according to formula (I).

The various stereoisomers can include geometric isomers, diastereomers and enantiomers. Thus, the compositions of the present invention can include compounds of racemic mixtures, individual stereoisomers and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

As a more particular example regarding stereoisomers, the {1-[6-(trifluoromethyl)pyridin-3-yl]ethyl]methyl}oxido-λ$^4$-sulfanylidenecyanamide compound described in Example I includes four separate stereoisomers. These four stereoisomers define two pairs of diastereomers, which for the purposes of this document are labeled as diastereomer groups (A) and (B). Diastereomer group (A) is defined by {(R)-1-[6-(trifluoromethyl)pyridin-3-yl]ethyl}-(R)-(methyl)oxido-λ$^4$-sulfanylidenecyanamide (A$^1$) and {(S)-1-[6-(trifluoromethyl)pyridin-3-yl]ethyl}-(5)-(methyl)oxido-λ$^4$-sulfanylidenecyanamide (A$^2$) as represented below.

Diastereomer Group A

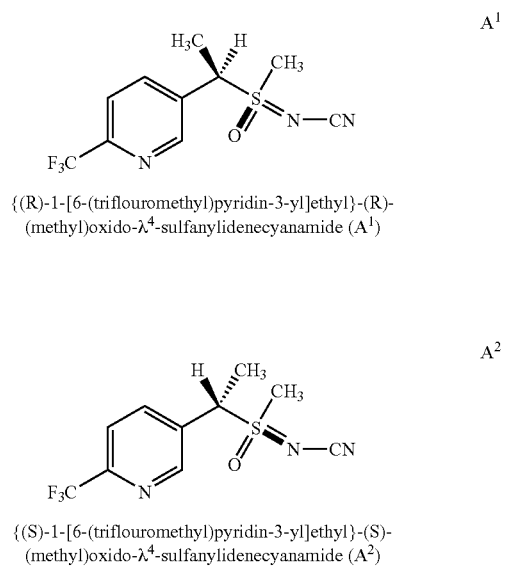 [SMILES: C[C@H](c1ccc(C(F)(F)F)nc1)S(C)(=O)=NC#N ; C[C@@H](c1ccc(C(F)(F)F)nc1)S(C)(=O)=NC#N]

Diastereomer group (B) is defined by {(R)-1-[6-(trifluoromethyl)pyridin-3-yl]ethyl}-(S)-(methyl)oxido-λ$^4$-sulfanylidenecyanamide (B$^1$) and {(S)-1-[6-(trifluoromethyl)pyridin-3-yl]ethyl}-(R)-(methyl)oxido-λ$^4$-sulfanylidenecyanamide (B$^2$) as represented below.

Diastereomer Group B

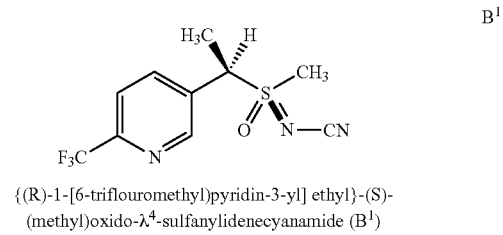

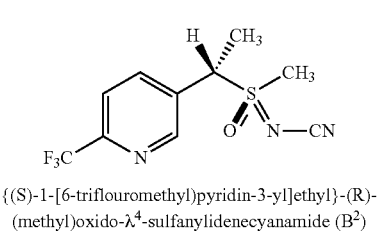

{(S)-1-[6-triflouromethyl)pyridin-3-yl]ethyl}-(R)-(methyl)oxido-$\lambda^4$-sulfanylidenecyanamide ($B^2$)

For compositions including a mixture of stereoisomers of a compound according to formula (I), conversion between the stereoisomers over time is contemplated, thereby resulting in ratios between the stereoisomers that are distinct from an initial ratio of the stereoisomers following synthesis of the compound. As a more particular example, following the initial synthesis of the {1-[6-(trifluoromethyl)pyridin-3-yl]ethyl}(methyl)oxido-$\lambda^4$-sulfanylidenecyanamide compound, diastereomer groups (A) and (B) are present in an approximate 1:2 mixture. However, it has been observed that conversion between diastereomer groups (A) and (B) is possible over time, thereby presenting various chemical and physical stability issues with respect to a composition containing the {1-[6-(trifluoromethyl)pyridin-3-yl]ethyl}(methyl)oxido-$\lambda^4$-sulfanylidenecyanamide compound. Methods for selectively controlling the conversion between stereoisomers of a compound according to formula (I) in a composition including a stereoisomeric mixture of the compound have now been surprisingly discovered. For example, in one form, a conversion between stereoisomers present in a composition at a first ratio is accelerated by heating the composition in a manner effective to yield a second ratio between the stereoisomers that is distinct from the first ratio. In one particular example of this form, the heating is performed at a minimum of about 10° C. for at least about 4 hours. In another example, the heating is performed at a minimum of about 20° C. for at least about 4 hours. In yet another example, the heating is performed at a minimum of about 30° C. for at least about 4 hours. In still another example, the heating is performed at a minimum of about 40° C. for at least about 4 hours. In another example, the heating is performed at a minimum of about 50° C. for at least about 4 hours. In yet another example, the heating is performed at a minimum of about 60° C. for at least about 4 hours. In a further example, the heating is performed at a minimum of about 70° C. for at least about 4 hours. In yet another example, the heating is performed at a minimum of about 80° C. for at least about 4 hours. In still another example, the heating is performed at a minimum of about 90° C. for at least about 4 hours. In another example, the heating is performed at a minimum of about 100° C. for at least about 4 hours.

Still, other variations in the temperature and time at which the heating are performed are contemplated. For example, in one or more forms, it is contemplated that the heating can be performed at one of the temperatures specified above but for an alternative period of time, such as from about 1 to about 100 hours. In a more particular form, the heating is performed at one of the above temperatures from about 2 to about 90 hours. In another form, the heating is performed at one of the above temperatures from about 4 to about 72 hours. In another variant, it is contemplated that the heating could be performed at a temperature up to a point just below the degradation or melting point of the compound according to formula (I) in the composition, thereby avoiding degradation of the compound during heating. As one non-limiting example, when the composition includes the {1-[6-(trifluoromethyl)pyridin-3-yl]ethyl}(methyl)oxido-$\lambda^4$-sulfanylidenecyanamide compound, the heating should be performed at a temperature less than about 128° C., which is the lower of the two melting points for diastereomer groups A and B.

In another more particular example, the heating is performed from 23-70° C. for a period from 4-72 hours. In another example, the heating is performed at 23° C. for at least about four hours. In yet another example, the heating is performed at about 54° C. for a period from 24-72 hours. In still another example, the heating is performed at about 70° C. for a period from 4-72 hours. In a further variant of this example, the period is selected from one of 4, 8, 24 and 72 hours. Still, other variations in the temperature and time at which the heating are performed are contemplated. For example, it is contemplated that as the value for one of the temperature and period of time at which the heating is performed changes, the value for the other of the temperature and period of time at which the heating is performed may also change.

In one or more forms, it is contemplated that the heating can be performed before the formulation of the composition is complete. For example, in one embodiment, a composition that includes a stereoisomeric mixture of a compound according to formula (I) and is substantially free of other materials is heated to obtain the desired conversion between stereoisomers. One or more additional materials may then be added to the composition, such as a(n) phytologically-acceptable carrier, wetting agent, thickener, insecticide or antifreeze, just to name a few possibilities. In an alternative embodiment, a composition that includes a stereoisomeric mixture of a compound according to formula (I) and at least one other insecticide, and is substantially free of other materials, is heated to obtain the desired conversion between stereoisomers. One or more additional materials may then be added to the composition, such as a phytologically-acceptable carrier, wetting agent, thickener or antifreeze, just to name a few examples. However, other variations in the order in which the compositions described herein may be prepared are contemplated. For example, in one or more forms, the formulation of the composition can be complete before it is heated. In addition to the foregoing, it should be appreciated that the composition can be subjected to further processing after the heating, including for example, bead milling to reduce particle size of the composition.

In one embodiment, the stereoisomers of the compound according to formula (I) define two pairs of diastereomers and the heating converts at least a portion of one pair of the diastereomers to the other pair of the diastereomers, thereby changing the ratio between the diastereomers of the compound present in the composition. In one more particular form, the ratio between the pairs of diastereomers after heating is at least about 3:1. In another form, the ratio between the pairs of diastereomers after heating is greater than about 10:1. In yet another form, the ratio between the pairs of diastereomers after heating is greater than about 20:1. In still another form, the ratio between the pairs of diastereomers after heating is greater than about 30:1. In another form, the ratio between the pairs of diastereomers after heating is greater than about 40:1. In a further form, the ratio between the pairs of diastereomers after heating is greater than about 50:1. In another form, the ratio between the pairs of diastereomers after heating is greater than about 60:1. In still another form, the ratio between the pairs of diastereomers after heating is greater than about 70:1. In yet another form, the ratio between the pairs of diastereomers after heating is greater than about 80:1. In another form, the ratio between the pairs of diastereomers after heating is greater than about 90:1. In still another form, the ratio between the pairs of diastereomers after heating is at least about 100:1. In another form, it is contemplated that only one pair of diastereomers remains after heating.

In another particular form, the ratio between the pairs of diastereomers after heating is from about 3:1 to about 100:1. In yet another form, the ratio between the pairs of diastereomers after heating is from about 3:1 to about 50:1. In another form, the ratio between the pairs of diastereomers after heating is from about 3:1 to about 40:1. Still, in another form, the ratio between the pairs of diastereomers after heating is from about 3:1 to about 39:1. In yet another form, the ratio between the pairs of diastereomers after heating is from about 19:1 to about 39:1. In another form, the ratio between the pairs of diastereomers after heating is from about 25:1 to about 39:1. Still, in other forms, the ratio between the pairs of diastereomers after heating is about 39:1. It should be appreciated however that further variations of the ratio between the pairs of the diastereomers are contemplated.

In another embodiment, a composition includes a compound according to formula (I) in a stereoisomeric mixture defined by two pairs of diastereomers. In one form, the mixture includes, based on the total weight of the stereoisomeric mixture in the composition, a first pair of diastereomers from about 50 to about 98 weight percent and a second pair of diastereomers from about 2 to about 50 weight percent. In another form, the mixture includes, based on the total weight of the stereoisomeric mixture in the composition, a first pair of diastereomers from about 60 to about 98 weight percent and a second pair of diastereomers from about 2 to about 40 weight percent. In yet another form, the mixture includes, based on the total weight of the stereoisomeric mixture in the composition, a first pair of diastereomers from about 75 to about 98 weight percent and a second pair of diastereomers from about 2 to about 25 weight percent. In a further form, the mixture includes, based on the total weight of the stereoisomeric mixture in the composition, a first pair of diastereomers from about 85 to about 98 weight percent and a second pair of diastereomers from about 2 to about 15 weight percent. Still, in another form the mixture includes, based on the total weight of the stereoisomeric mixture in the composition, a first pair of diastereomers from about 90 to about 98 weight percent and a second pair of diastereomers from about 2 to about 10 weight percent. In another form, the mixture includes, based on the total weight of the stereoisomeric mixture in the composition, a first pair of diastereomers from about 95 to about 98 weight percent and a second pair of diastereomers from about 2 to about 5 weight percent. In yet another form, the mixture includes, based on the total weight of the stereoisomeric mixture in the composition, a first pair of the diastereomers at about 99 weight percent and a second pair of diastereomers at about 1 weight percent. In a further form, the mixture includes, based on the total weight of the stereoisomeric mixture in the composition, about 100 weight percent of a first pair of the diastereomers.

In one particular form of this embodiment, the compound according to formula (I) is {1-[6-(trifluoromethyl)pyridin-3-yl]ethyl}(methyl)oxido-$\lambda^4$-sulfanylidenecyanamide and the first pair of stereoisomers is defined by {(R)-1-[6-(trifiouromethyl)pyridin-3-yl]ethyl}-(R)-(methyl)oxido-$\lambda^4$-sulfanylidenecyanamide and {(S)-1-[6-(trifluoromethyl)pyridin-3-yl]ethyl}-(S)-(methyl)oxido-$\lambda^4$-sulfanylidenecyanamide and the second pair of diastereomers is defined by {(R)-1-[6-(trifluoromethyl)pyridin-3-yl]ethyl}-(S)-(methyl)oxido-$\lambda^4$-sulfanylidenecyanamide and {(S)-1-[6-(trifluoromethyl)pyridin-3-yl]ethyl}-(R)-(methyl)oxido-$\lambda^4$-sulfanylidenecyanamide. In a further variation of this form, the stereoisomeric mixture having one of the foregoing weight percentages of diastereomers is prepared by heating the composition at a temperature from about 20-70° C. for a period from about 4-72 hours. Additionally or alternatively, it is contemplated that one or more other insecticides can be included in this form. As one example, the composition can include a spinosyn, such as spinetoram, spinosad or mixtures thereof. When present, the composition can include a ratio, by weight, between {1-[6-(trifluoromethyl)pyridin-3-yl]ethyl}(methyl)oxido$\lambda^4$-sulfanylidenecyanamide and the spinosyn from about 1:10 to about 10:1. In another form, the composition can include a ratio, by weight, between {1-[6-(trifluoromethyl)pyridin-3-yl]ethyl}(methyl)oxido$\lambda^4$-sulfanylidenecyanamide and the spinosyn from about 1:5 to about 5:1. In yet another form, the composition can include a ratio, by weight, between {1-[6-(trifluoromethyl)pyridin-3-yl]ethyl}(methyl)oxido$\lambda^4$-sulfanylidenecyanamide and the spinosyn from about 1:3 to about 3:1. In still another form, the composition can include a ratio, by weight, between {1-[6-(trifluoromethyl)pyridin-3-yl]ethyl}(methyl)oxido-$\lambda^4$-sulfanylidenecyanamide and the spinosyn from about 2:1 to about 2.4:1.

While the mixture of {1-[6-(trifluoromethyl)pyridin-3-yl]ethyl}(methyl)oxido-$\lambda^4$-sulfanylidenecyanamide and an insecticide, such as a spinosyn, has been described above, it should be appreciated that in certain embodiments a composition can include any compound according to formula (I) and one or more other insecticides. For example, these compositions could include a compound according to formula (I) and a spinosyn, such as spinetoram, spinosad or mixtures thereof. When present, these compositions can include a ratio by weight between the compound according to formula (I) and the insecticide from about 1:10 to about 10:1. In another form, these compositions can include a ratio by weight between the compound according to formula (I) and the insecticide from about 1:5 to about 5:1. In still another form, these compositions can include a ratio by weight between the compound according to formula (I) and the insecticide from about 1:3 to about 3:1.

The compositions of this invention may also be provided with a phytologically-acceptable inert carrier in the form of sprays, topical treatments, gels, seed coatings, microcapsulations, systemic uptake, baits, eartags, boluses, foggers, fumigants aerosols, dusts and many others. Typically, formulations are applied as aqueous suspensions or emulsions. Such suspensions or emulsions are produced from water-soluble, water suspendable, or emulsifiable formulations which are (1) solids, usually known as wettable powders or water dispersible granules or (2) liquids, usually known as emulsifiable concentrates, aqueous emulsions, suspension concentrates and water suspended capsules containing the composition. As will be readily appreciated, any material to which the composition can be added may be used, provided they yield the desired utility without significant interference with the activity of the composition as a pesticide.

Wettable powders, which may be compacted, extruded or processed through a dispersion in water followed by spray drying or fluid bed agglomeration to form water dispersible granules, comprise an intimate mixture of the composition, an inert carrier and surfactants. The concentration of the composition in the wettable powder is usually from 10 percent to 90 percent by weight based on the total weight of the wettable powder, more preferably 25 weight percent to 75 weight percent. In the preparation of wettable powder formulations, the composition can be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the composition and milled.

Emulsifiable concentrates of the composition comprise a convenient concentration, such as from 5 weight percent to 75 weight percent of the composition, in a suitable liquid, based on the total weight of the concentrate. The composition is dissolved in an inert carrier, which is either water, a water miscible solvent, a water immiscible solvent, or a mixture thereof and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyokyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulfated polyglycol ethers and appropriate salts of phosphated polyglycol ether.

Representative organic liquids which can be employed in preparing the emulsifiable concentrates of the composition are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol and the like. Mixtures of two or more organic liquids may also be employed in the preparation of the emulsifiable concentrate. Preferred organic liquids include xylene, and propyl benzene fractions, with propylbenzene fractions being most preferred. Surface-active emulsifying agents are typically employed in liquid formulations and in an amount of from 0.1 to 20 percent by weight based on the combined weight of the emulsifying agent with the composition. The formulations comprising the composition of the present invention can also contain other compatible additives, for example, miticides, insecticides, plant growth regulators, other fungicides, and other biologically active compounds used in agriculture.

Aqueous suspensions comprise suspensions of the composition, dispersed in an aqueous vehicle at a concentration in the range from 5 to 50 weight percent, based on the total weight of the aqueous suspension. Aqueous suspensions are prepared by vigorously mixing the composition of the present invention, or its solution, into a vehicle comprised of water and surfactants chosen from the same types discussed above. Other components, such as inorganic salts and synthetic or natural gums, may also be added to increase the density and viscosity of the aqueous vehicle. Examples of aqueous suspensions include suspensions of oil droplets (EW's), solids (SC's), and capsules (CS's).

The composition can also be applied as granular formulations, which are particularly useful for applications to the soil. Granular formulations usually contain from 0.5 to 10 weight percent, based on the total weight of the granular formulation of the composition, dispersed in an inert carrier which consists entirely or in large part of coarsely divided inert material such as attapulgite, bentonite, diatomite, clay or a similar inexpensive substance. Such formulations are usually prepared by diluting the composition in a suitable solvent and applying it to a granular carrier which has been preformed to the appropriate particle size, in the range of from 0.5 to 3 mm. A suitable solvent is a solvent in which the compound is substantially or completely soluble. Such formulations may also be prepared by making a dough or paste of the carrier and the composition and solvent, and crushing and drying to obtain the desired granular particle.

The composition of the present invention can also be applied as a water dispersible granule, or dry flowable formulation. Water dispersible granules typically contain from 10 to 70 percent of the composition, based on the total weight of the formulation. Such formulations are typically obtained through mixing and/or spraying the mixture onto a carrier with the addition of a dispersing and/or wetting agent, and combining with water to form a mixture suitable for further processing using well known granulation technologies, such as pan granulation, extrusion, spray-drying, fluid bed agglomeration, and the like.

Dusts containing the composition can be prepared by intimately mixing the composition with a suitable dusty agricultural carrier, such as, for example, kaolin clay, ground volcanic rock, and the like. Dusts can suitably contain from 1 to 10 weight percent of the composition, based on the total weight of the dust. Dusts may also be prepared by impregnating the composition onto a carrier in a similar manner to that described for granules above.

The formulations of the present invention may additionally contain adjuvant surfactants to enhance deposition, wetting and penetration of the composition onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

EXAMPLE IX

Preparation of Composition Including a Stereoisomeric Mixture of {1-[6-(trifluoromethyl)pyridin-3-yl]ethyl}(methyl)oxido-$\lambda^4$-sulfanylidenecyanamide A 1 liter total volume (~1100 g total weight) of a suspension concentrate product having a 240 g/L concentration of {1-[6-(trifluoromethyl)pyridin-3-yl]ethyl}(methyl)oxido-$\lambda^4$-sulfanylidenecyanamide with an approximate 1:2 ratio between diastereomer groups A and B was prepared by first adding deionized water to a clean beaker equipped with a mechanical stirrer. The following ingredients were then added to the beaker, in no particular, under continued stirring: 3.5 g of Agnique® DFM 112S, a silicon based defoamer available commercially from the Cognis Group, headquartered in Monheim, Germany; 20 g of Tersperse® 2500, a polymeric surfactant commercially available from Huntsman Performance Products, 10003 Woodloch Forest Drive, The Woodlands, Tex. 77380; 30 g of Morwet® D-360, a surfactant commercially available from Akzo Nobel Surfactants, 525 W. Van Buren St., Chicago, Ill. 60607; 20 g of Ethylan® NS 500 LQ, a surfactant commercially available from Akzo Nobel Surfactants, 525 W. Van Buren St., Chicago, Ill. 60607; 40 g of propylene glycol; 1 g of Proxel® GXL, a microbiostat solution commercially available from Arch Chemicals, Inc., 1955 Lake Drive, Suite 100, Smyrna, Ga. 30080. 240 g of {1-[6-(trifluoromethyl)pyridin-3-yl]ethyl}(methyl)oxido-$\lambda^4$-sulfanylidenecyanamide was then added to the beaker, followed by the addition of 10 g of Avicel® CL-611, a stabilizer commercially available from FMC BioPolymer, 1735 Market Street, Philadelphia, Pa. 19103, and 2 g of Kelzan, a xanthan gum commercially available from CP Kelco, 1000 Parkwood Circle, Suite 1000, Atlanta, Ga. 30339. The ingredients were stirred until a homogeneous mixture was obtained. The mixture was then milled with a bead mill down to an average particle size of 3-5 µm. The final formulation of this suspension concentrate product is set forth in Table 1.

TABLE 1

| Ingredients | g/L |
| --- | --- |
| {1-[6-(trifluoromethyl)pyridin-3-yl]ethyl}(methyl)oxido-$\lambda^4$-sulfanylidenecyanamide | 240 |
| Agnique ® DFM 112S | 3.5 |
| Avicel ® CL-611 | 10 |
| Terspserse ® 2500 | 20 |
| Morwet ® D-360 | 30 |
| Ethylan ® NS 500 LQ | 20 |
| Propylene glycol | 40 |
| Proxel ® GXL | 1 |
| Kelzan ® | 2 |
| Water | balance |

A composition having a 160 mL total volume was prepared by combining 80 mL of the suspension concentrate product described above having a 240 g/L concentration of {1-[6-(trifluoromethyl)pyridin-3-yl]ethyl}(methyl)oxido-$\lambda^4$-sulfanylidenecyanamide and 80 mL of Radiant® SC, an insecticide formulation having a 120 g/L concentration of spinetoram and being commercially available from Dow AgroSciences, LLC, 9330 Zionsville Road, Indianapolis, Ind. 46268. The composition was thoroughly mixed until a homogenous consistency was obtained. Sixteen individual 10 mL samples (samples (i)-(xvi)) of the composition were then heated in an oven in accordance with the time and temperature parameters set forth in Table 2 below.

TABLE 2

| | Heating Parameters | | | |
| --- | --- | --- | --- | --- |
| | 4 hrs | 8 hrs | 24 hrs | 72 hrs |
| 23° C. | (i) | (v) | (ix) | (xiii) |
| 40° C. | (ii) | (vi) | (x) | (xiv) |
| 54° C. | (iii) | (vii) | (xi) | (xv) |
| 70° C. | (iv) | (viii) | (xii) | (xvi) |

Upon expiration of the respective time periods set forth in Table 2, the samples were removed from the oven and subsequently assayed by chromatography to measure the ratio between diastereomer groups A and B of {1-[6-(trifluoromethyl)pyridin-3-yl]ethyl}(methyl)oxido-$\lambda^4$-sulfanylidenecyanamide in each sample after heating. The results of the chromatography analysis are provided in Table 3, which also indicates the pH of each sample and the percent by weight, based on the total weight of the respective sample, of {1-[6-(trifluoromethyl)pyridin-3-yl]ethyl}(methyl)oxido-$\lambda^4$-sulfanylidenecyanamide and spinetoram.

TABLE 3

Diastereomer ratios of {1-[6-(trifluoromethyl)pyridin-3-yl]ethyl}(methyl)oxido-$\lambda^4$-sulfanylidenecyanamide in samples (i)-(xvi) after heating.

| | | {1-[6-(trifluoromethyl)pyridin-3-yl]ethyl}(methyl)oxido-$\lambda^4$-sulfanylidenecyanamide | | | Spinetoram |
| --- | --- | --- | --- | --- | --- |
| Sample | pH | Diastereomer (A) % | Diastereomer (B) % | Total Assay, % w/w | Total Assay, % w/w |
| (i) | 7.23 | 50.74 | 49.26 | 10.967 | 4.562 |
| (ii) | 7.20 | 53.33 | 46.67 | 10.981 | 4.574 |
| (iii) | 7.23 | 62.63 | 37.37 | 10.913 | 4.567 |
| (iv) | 7.28 | 94.98 | 5.02 | 10.722 | 4.557 |
| (v) | 7.23 | 50.95 | 49.05 | 10.953 | 4.564 |
| (vi) | 7.18 | 55.26 | 44.74 | 10.844 | 4.520 |
| (vii) | 7.21 | 74.02 | 25.98 | 10.786 | 4.548 |
| (viii) | 7.23 | 95.55 | 4.45 | 10.677 | 4.556 |
| (ix) | 7.20 | 51.52 | 48.48 | 10.975 | 4.569 |
| (x) | 7.16 | 63.31 | 36.69 | 10.887 | 4.576 |
| (xi) | 7.16 | 97.03 | 2.97 | 10.697 | 4.577 |
| (xii) | 7.21 | 95.18 | 4.82 | 10.710 | 4.541 |
| (xiii) | 7.16 | 53.38 | 46.62 | 11.035 | 4.595 |
| (xiv) | 7.15 | 86.06 | 13.94 | 10.832 | 4.598 |
| (xv) | 7.17 | 97.51 | 2.49 | 10.768 | 4.613 |
| (xvi) | 7.24 | 96.15 | 3.85 | 10.766 | 4.614 |

It should be appreciated that the foregoing Examples are for illustration purposes and are not intended to be construed as limiting the invention disclosed in this document to only the embodiments disclosed in these examples. For example, it is contemplated that the {1-[6-(trifluoromethyl)pyridin-3-yl]ethyl}(methyl)oxido-$\lambda^4$-sulfanylidenecyanamide compound in the exemplary composition could be replaced with one or a mixture of the compounds according to formula (I). Similarly, it is contemplated that the exemplary composition could be prepared with one or more co-ingredients in addition to or in lieu of spinetoram, or alternatively, may be free from any co-ingredients.

Insecticide Utility

The compositions disclosed in this document are useful for the control of invertebrates including insects. Therefore, the present invention also is directed to a method for inhibiting an insect which comprises applying an insect-inhibiting amount of the composition to a locus of the insect, to the area to be protected, or directly on the insect to be controlled. The compositions of the invention may also be used to control other invertebrate pests such as mites and nematodes.

The "locus" of insects or other pests is a term used herein to refer to the environment in which the insects or other pests live or where their eggs are present, including the air surrounding them, the food they eat, or objects which they contact. For example, insects which eat, damage or contact edible, commodity, ornamental, turf or pasture plants can be controlled by applying the compositions to the seed of the plant before planting, to the seedling, or cutting which is planted, the leaves, stems, fruits, grain, and/or roots, or to the soil or other growth medium before or after the crop is planted. Protection of these plants against virus, fungus or bacterium diseases may also be achieved indirectly through controlling sap-feeding pests such as whitefly, plant hopper, aphid and spider mite. Such plants include those which are bred through conventional approaches and which are genetically modified using modern biotechnology to gain insect-resistant, herbicide-resistant, nutrition-enhancement, and/or any other beneficial traits.

It is contemplated that the compositions might also be useful to protect textiles, paper, stored grain, seeds and other foodstuffs, houses and other buildings which may be occupied by humans and/or companion, farm, ranch, zoo, or other animals, by applying an active composition to or near such objects. Domesticated animals, buildings or human beings might be protected with the compositions by controlling invertebrate and/or nematode pests that are parasitic or are capable of transmitting infectious diseases. Such pests include, for example, chiggers, ticks, lice, mosquitoes, flies, fleas and heartworms. Nonagronomic applications also include invertebrate pest control in forests, in yards, along road sides and railroad right of way.

The term "inhibiting an insect" refers to a decrease in the numbers of living insects, or a decrease in the number of viable insect eggs. The extent of reduction accomplished by a composition depends, of course, upon the application rate of the composition, the particular composition used, and the target insect species. At least an inactivating amount should be used. The term "insect-inactivating amount" is used to describe the amount, which is sufficient to cause a measurable reduction in the treated insect population. Generally an amount in the range from about 1 to about 1000 ppm by weight active compound is used. For example, insects or other pests which can be inhibited include, but are not limited to:

Lepidoptera—*Heliothis* spp., *Helicoverpa* spp., *Spodoptera* spp., *Mythimna unipuncta*, *Agrotis ipsilon*, *Earias* spp., *Euxoa auxiliaris*, *Trichoplusia ni*, *Anticarsia gemmatalis*, *Rachiplusia nu*, *Plutella xylostella*, *Chilo* spp., *Scirpophaga incertulas*, *Sesamia* inferens, *Cnaphalocrocis medinalis*, *Ostrinia nubilalis*, *Cydia pomonella*, *Carposina niponensis*, *Adoxophyes orana*, *Archips argyrospilus*, *Pandemis heparana*, *Epinotia aporema*, *Eupoecilia ambiguella*, *Lobesia botrana*, *Polychrosis viteana*, *Pectinophora gossypiella*, *Pieris rapae*, *Phyllonorycter* spp., *Leucoptera malifoliella*, *Phyllocnisitis citrella Coleoptera Diabrotica* spp., *Leptinotarsa decemlineata*, *Oulema oryzae*, *Anthonomus grandis*, *Lissorhoptrus oryzophilus*, *Agriotes* spp., *Melanotus communis*, *Popillia japonica*, *Cyclocephala* spp., *Tribolium* spp.

Homoptera—*Aphis* spp., *Myzus persicae*, *Rhopalosiphum* spp., *Dysaphis plantaginea*, *Toxoptera* spp., *Macrosiphum euphorbiae*, *Aulacorthum solani*, *Sitobion avenae*, *Metopolophium dirhodum*, *Schizaphis graminum*, *Brachycolus noxius*, *Nephotettix* spp., *Nilaparvata lugens*, *Sogatella furcifera*, *Laodelphax striatellus*, *Bemisia tabaci*, *Trialeurodes vaporariorum*, *Aleurodes proletella*, *Aleurothrixus floccosus*, *Quadraspidiotus perniciosus*, *Unaspis yanonensis*, *Ceroplastes rubens*, *Aonidiella* aurantii Hemiptera—*Lygus* spp., *Eurygaster maura*, *Nezara viridula*, *Piezodorus guildingi*, *Leptocorisa varicornis*, *Cimex lectularius*, *Cimex hemipterus*

Thysanoptera—*Frankliniella* spp., *Thrips* spp., *Scirtothrips dorsalis*

Isoptera—*Reticulitermes flavipes*, *Coptotermes formosanus*, *Reticulitermes virginicus*, *Heterotermes aureus*, *Reticulitermes hesperus*, *Coptotermes frenchii*, *Shedorhinotermes* spp., *Reticulitermes santonensis*, *Reticulitermes grassei*, *Reticulitermes* banyulensis, *Reticulitermes speratus*, *Reticulitermes hageni*, *Reticulitermes tibialis*, *Zootermopsis* spp., *Incisitermes* spp., *Marginitermes* spp., *Macrotermes* spp., *Microcerotermes* spp., *Microtermes* spp.

Diptera—*Liriomyza* spp., *Musca domestica*, *Aedes* spp., *Culex* spp., *Anopheles* spp., *Fannia* spp., *Stomoxys* spp.

Hymenoptera—*Iridomyrmex humilis*, *Solenopsis* spp., *Monomorium pharaonis*, *Atta* spp., *Pogonomyrmex* spp., *Camponotus* spp., *Monomorium* spp., *Tapinoma sessile*, *Tetramorium* spp., *Xylocapa* spp., *Vespula* spp., *Polistes* spp.

Mallophaga (chewing lice)

Anoplura (sucking lice)—*Pthirus pubis*, *Pediculus* spp.

Orthoptera (grasshoppers, crickets)—*Melanoplus* spp., *Locusta migratoria*, *Schistocerca gregaria*, *Gryllotalpidae* (mole crickets).

Blattoidea (cockroaches)—*Blatta orientalis*, *Blattella germanica*, *Periplaneta americana*, *Supella longipalpa*, *Periplaneta australasiae*, *Periplaneta brunnea*, *Parcoblatta pennsylvanica*, *Periplaneta fuliginosa*, *Pycnoscelus surinamensis*, Siphonaptera—*Ctenophalides* spp., *Pulex* irritans Acari—*Tetranychus* spp., *Panonychus* spp., *Eotetranychus carpini*, *Phyllocoptruta oleivora*, *Aculus pelekassi*, *Brevipalpus phoencis*, *Boophilus* spp., *Dermacentor variabilis*, *Rhipicephalus sanguineus*, *Amblyomma americanum*, *Ixodes* spp., *Notoedres cati*, *Sarcoptes scabiei*, *Dermatophagoides* spp.

Nematoda—*Dirofilaria immitis*, *Meloidogyne* spp., *Heterodera* spp., *Hoplolaimus columbus*, *Belonolaimus* spp., *Pratylenchus* spp., *Rotylenchus reniformis*, *Criconemella ornata*, *Ditylenchus* spp., *Aphelenchoides besseyi*, *Hirschmanniella* spp.

The actual amount of composition to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a composition is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Systemic movement of compositions of the invention in plants may be utilized to control pests on one portion of the plant by applying the compositions to a different portion of it. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal proteins, those expressing herbicide resistance, such as "Roundup Ready®" seed, or those with "stacked" foreign genes expressing insecticidal proteins, herbicide resistance, nutrition-enhancement and/or any other beneficial traits.

The composition can also be provided as an insecticidal bait formulation including attractants and/or feeding stimulants that may be used to increase efficacy of the compositions against insect pest in a device such as trap, bait station, and the like. The bait formulation is usually a solid, semi-solid (including gel) or liquid bait matrix including the stimulants and one or more non-microencapsulated or microencapsulated insecticides in an amount effective to act as kill agents.

The compositions of the present invention are often applied in conjunction with one or more other insecticides or fungicides or herbicides to obtain control of a wider variety of pests diseases and weeds. When used in conjunction with other insecticides or fungicides or herbicides, the presently claimed compositions can be formulated with the other insecticides or fungicides or herbicide, tank mixed with the other insecticides or fungicides or herbicides, or applied sequentially with the other insecticides or fungicides or herbicides.

Some of the insecticides that can be employed beneficially in combination with the compositions of the present invention include: antibiotic insecticides such as allosamidin and thuringiensin; macrocyclic lactone insecticides such as spinosad, spinetoram, and other spinosyns including the 21-butenyl spinosyns and their derivatives; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; biological insecticides such as *Bacillus popilliae, B. sphaericius, B. thurinigiensis* subsp. *aizqwai, B. thuringiensis* subsp. *kurstaki, B. thuriugiensis* subsp. *tenebrionis, Beauveria bassiana, Cydia pomonella granulosis* virus, Douglas fir tussock moth NPV, gypsy moth NPV, *Helicoverpa zea* NPV, Indian meal moth granulosis virus, *Metarhizium anisopliae, Nosema locustae, Paecilomyces fumosoroseus, P. lilacinus, Photorhabdus luminescens, Spodoptera exigua* NPV, trypsin modulating oostatic factor, *Xenorhabdus nematophilus*, and X. bovienii; plant incorporated protectant insecticides such as Cry1Ab, Cry1Ac, Cry1F, Cry1A.105, Cry2Ab2, Cry3A, mir Cry3A, Cry3Bb1, Cry34, Cry35, and VIP3A; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as am itraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, PSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temnephos, trichlormetaphos-3 and trifenofos; phosphloiate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypertnethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spirodiclofen, spiromesifen and spirotetramat; thiourea insecticides such as diafenthiuron; urea insecticides such as flucofuron and sulcofuron; and unclassified insecticides such as AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene and triazamate and any combinations thereof.

Some of the fungicides that can be employed beneficially in combination with the compositions of the present invention include: 2-(thiocyanatomethylthio)-benzothiazole, 2-phenylphenol, 8-hydroxyquinoline sulfate, Ampelomyces, quisqualis, azaconazole, azoxystrobin, Bacillus subtilis, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, Coniothyrium minitans, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, Candida oleophila, Fusarium oxysporum, Gliocladium spp., Phlebiopsis gigantean, Streptomyces griseoviridis, Trichoderma spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, mycozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

Some of the herbicides that can be employed in conjunction with the compositions of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchior, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmediphamethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diplhenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolyiplpiethyl herbicides such as fluazolate and pyraflufen; pyridamine herbicides such as credazine, pyridafol and pyridate; pyridazitiotte herbicides such as brompyrazon, chloridazon, dimidazon, flufenpyr, metflurazon, norflurazon, oxapyrazon and pydanon; pyridinie herbicides such as aminopyralid, cliodinate, clopyralid, dithiopyr, fluoroxypyr, haloxydine, picloram, picolinafen, pyriclor, thiazopyr and triclopyr; pyrimidinediamitie herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EP,TC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

Before an insecticide can be used or sold commercially, such composition undergoes lengthy evaluation processes by various governmental authorities (local, regional, state, national, and international). Voluminous data requirements are specified by regulatory authorities and must be addressed through data generation and submission by the product registrant or by another on the product registrant's behalf. These governmental authorities then review such data and if a determination of safety is concluded, provide the potential user and/or seller with product registration approval. Thereafter, in that locality where the product registration is granted and supported, such user and/or seller may use and/or sell such compound.

Any theory, mechanism of operation, proof, or finding stated herein is meant to further enhance understanding of the present invention and is not intended to make the present invention in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary. While the invention has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A method, comprising:
providing a composition including a stereoisomeric mixture of a compound having the following structure:

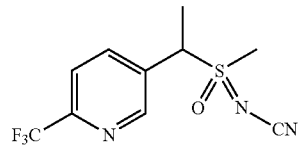

wherein
the mixture is defined by a first pair of diastereomers and a second pair of diastereomers, the first pair of diastereomers being defined by {(R)-1-[6-(triflouromethyl)pyridin-3-yl]ethyl}-(R)-(methyl)oxido-$\lambda^4$-sulfanylidenecyanamide and {(S)-1-[6-(triflouromethyl)pyridin-3-yl]ethyl}-(S)(methyl)oxido-$\lambda^4$-sulfanylidenecyanamide and the second pair of diastereomers being defined by {(R)-1-[6-(triflouromethyl)pyridin-3-yl]ethyl}-(S)-(methyl)oxido-$\lambda^4$-sulfanylidenecyanamide and {(S)-1-[6-(triflouromethyl)pyridin-3-yl]ethyl}-(R)-(methyl)oxido-$\lambda^4$-sulfanylidenecyanamide; and
heating the composition to convert at least a portion of the second pair of diastereomers to the first pair of diastereomers.

2. The method of claim 1, wherein the heating is performed at a minimum of about 50 ° C. from about four to about seventy two hours.

3. The method of claim 1, wherein the composition includes a spinosyn selected from the group consisting of spinetoram, spinosad and mixtures thereof.

* * * * *